(12) United States Patent  (10) Patent No.: US 9,352,137 B2
Simonton et al.  (45) Date of Patent: May 31, 2016

(54) DRUG CARTRIDGE FOR DELIVERING A DRUG DEPOT COMPRISING A BULKING AGENT AND/OR COVER

(75) Inventors: Thomas A. Simonton, Memphis, TN (US); John M. Zanella, Cordova, TN (US); Vanja King, Memphis, TN (US)

(73) Assignee: Warsaw Orthopedic, Inc., Warsaw, IN (US)

(*) Notice: Subject to any disclaimer, the term of this patent is extended or adjusted under 35 U.S.C. 154(b) by 1377 days.

(21) Appl. No.: 12/260,876

(22) Filed: Oct. 29, 2008

(65) Prior Publication Data

US 2010/0106133 A1 Apr. 29, 2010

(51) Int. Cl.
*A61M 37/00* (2006.01)
*A61M 31/00* (2006.01)

(52) U.S. Cl.
CPC ......... *A61M 37/0069* (2013.01); *A61M 31/007* (2013.01)

(58) Field of Classification Search
CPC .......... A61M 37/0069; A61M 37/007; A61M 31/007
USPC ...................................... 604/57–64
See application file for complete search history.

(56) References Cited

U.S. PATENT DOCUMENTS

| 4,105,030 | A |   | 8/1978  | Kercso            |
|-----------|---|---|---------|-------------------|
| 4,451,253 | A |   | 5/1984  | Harman            |
| 4,576,591 | A | * | 3/1986  | Kaye et al. ............ 604/62 |
| 5,024,655 | A |   | 6/1991  | Freeman et al.    |
| 5,207,678 | A |   | 5/1993  | Harms et al.      |
| 5,212,162 | A |   | 5/1993  | Missel et al.     |
| 5,694,920 | A | * | 12/1997 | Abrams et al. ........... 128/200.16 |
| 5,756,127 | A |   | 5/1998  | Grisoni et al.    |
| 6,132,420 | A | * | 10/2000 | Dionne et al. ............. 604/892.1 |
| 6,203,813 | B1 |   | 3/2001  | Gooberman         |
| 6,242,004 | B1 | * | 6/2001  | Rault ............................ 424/472 |
| 6,471,688 | B1 |   | 10/2002 | Harper et al.     |
| 6,478,776 | B1 |   | 11/2002 | Rosenman et al.   |
| 6,530,934 | B1 |   | 3/2003  | Jacobsen et al.   |
| 6,735,475 | B1 |   | 5/2004  | Whitehurst et al. |
| 6,971,998 | B2 |   | 12/2005 | Rosenman et al.   |
| 7,001,892 | B1 |   | 2/2006  | Chmielewski et al. |

(Continued)

OTHER PUBLICATIONS

Kawawada, Karen. WCI Student Isolates Microbe that Lunches on Plastic Bags. Sep. 1, 2009. Retrieved on Sep. 29, 2013 from http://woohooreport.com/2009/09/wci-student-isolates-microbe-that-lunches-on-plastic-bags/.*

(Continued)

*Primary Examiner* — Manuel Mendez
(74) *Attorney, Agent, or Firm* — Sorell Lenna & Schmidt LLP

(57) ABSTRACT

A drug cartridge is provided for delivering a drug pellet to a site beneath the skin of a patient, the drug cartridge comprising: two or more chambers, each chamber holding a drug pellet and having a proximal end and a distal end, the proximal end of the chamber having an opening to receive the drug pellet and a plunger, the distal end of the chamber having an opening for receiving the plunger and passage of the drug pellet, a bulking agent disposed within at least a portion of each chamber, wherein movement of the plunger to an extended position moves the drug pellet within the chamber of the cartridge out the distal end of the chamber and out of the drug cartridge. In some embodiments, instead or with the bulking agent pierceable superior and inferior covers are used to contain the drug pellets.

17 Claims, 9 Drawing Sheets

(56) References Cited

U.S. PATENT DOCUMENTS

| | | |
|---|---|---|
| 7,108,153 B2 * | 9/2006 | Wood .................... 221/15 |
| 7,252,651 B2 | 8/2007 | Haider et al. |
| 2001/0020147 A1 * | 9/2001 | Staniforth et al. .......... 604/58 |
| 2001/0041190 A1 * | 11/2001 | Ward et al. ................ 424/489 |
| 2001/0043915 A1 | 11/2001 | Frey |
| 2002/0082583 A1 * | 6/2002 | Lerner .................... 604/512 |
| 2004/0015133 A1 | 1/2004 | Karim |
| 2004/0064193 A1 | 4/2004 | Evans et al. |
| 2004/0111118 A1 | 6/2004 | Hill et al. |
| 2004/0220545 A1 | 11/2004 | Heruth et al. |
| 2004/0220546 A1 | 11/2004 | Heruth et al. |
| 2004/0220547 A1 | 11/2004 | Heruth et al. |
| 2004/0220548 A1 | 11/2004 | Heruth et al. |
| 2005/0070843 A1 | 3/2005 | Gonzales |
| 2005/0074481 A1 | 4/2005 | Brekke et al. |
| 2005/0137579 A1 | 6/2005 | Heruth et al. |
| 2005/0152949 A1 | 7/2005 | Hotchkiss et al. |
| 2005/0177118 A1 | 8/2005 | Hoganson et al. |
| 2005/0178779 A1 * | 8/2005 | Wood ........................ 221/7 |
| 2005/0245906 A1 | 11/2005 | Makower et al. |
| 2005/0249775 A1 | 11/2005 | Falotico et al. |
| 2006/0046961 A1 | 3/2006 | McKay et al. |
| 2006/0253100 A1 | 11/2006 | Burright et al. |
| 2006/0264839 A1 | 11/2006 | Veasey et al. |
| 2007/0055378 A1 | 3/2007 | Ankney et al. |
| 2007/0219564 A1 | 9/2007 | Rue et al. |
| 2008/0228193 A1 | 9/2008 | Matityahu |

OTHER PUBLICATIONS

Lupron Depot Package Insert, TAP Pharmaceutical Products Inc., pp. 1-10.

Norplant Package Insert, Wyeth Pharmaceuticals Inc., pp. 1-26.

* cited by examiner

DRUG CARTRIDGE FOR DELIVERING A DRUG DEPOT COMPRISING A BULKING AGENT AND/OR COVER

BACKGROUND

Drugs may be delivered to patients by a variety of methods including oral, intravenous, intramuscular, inhalation, topical, subcutaneous delivery or delivery directly or locally to the treatment site (e.g., intrathecally, intraspinally, intraarticularly, etc.). The method of delivery chosen depends, among other things, upon the condition being treated, desired therapeutic concentration of the drug to be achieved in the patient and the duration of drug concentration that must be maintained.

Recently, drug depots have been developed which allow a drug to be introduced or administered to sites beneath the skin of a patient so that the drug is slowly released over a long period of time. Such drug depots allow the drug to be released from the depot in a relatively uniform dose over weeks, months or even years. This method of administering drugs is becoming especially important and popular in modulating the immune, inflammation and/or pain responses in treatment of chronic conditions including rheumatoid arthritis, osteoarthritis, sciatica, carpal tunnel syndrome, lower back pain, lower extremity pain, upper extremity pain, cancer, tissue pain and pain associated with injury or repair of cervical, thoracic, and/or lumbar vertebrae or intervertebral discs, rotator cuff, articular joint, TMJ, tendons, ligaments, muscles, and the like.

Previously, drug depots and other types of implants have been inserted into the treatment site beneath the skin by use of a trocar device, which is a two-piece device that includes a cannula and an obdurator. The trocar device requires an incision to be made through the skin at the site of implant of the drug depot using a separate instrument (e.g., scalpel). A cannula and obdurator are inserted together through the skin at the incision site. Next, the obdurator is withdrawn, leaving the cannula in place as a guide for inserting the drug depot. The drug depot is inserted through the cannula, and the obdurator is used to push the implant to the end of the cannula. The cannula and obdurator are then withdrawn completely, leaving the implant in place beneath the skin.

Typically, trocar devices are used to implant drug depots subcutaneously over a large area (e.g., 2-2.5 inches), with a typical drug depot in the order of 1½ inches long. Thus, the trocar device is not suitable for many treatment sites because it lacks precision and may cause additional trauma to the tissue surrounding the site of implant.

Other drug depot devices have been developed to simplify implanting the drug depots. These devices have a handle for one-handed implantation of the drug depot, a needle containing the drug depot to be implanted and a rod positioned within the needle for pushing the drug depot out of the needle. Once the needle containing the drug depot has been inserted at the site of implant, a spring loaded trigger on the handle is activated which causes the needle to be automatically withdrawn by a spring leaving the implanted drug depot in place. Unfortunately, it is not possible to control the motion of the needle in these devices because the needle will automatically retract upon activation of the trigger. The complex spring loaded propelling system and trigger of these devices increase the chances that the device will jam and fail to eject the drug depot when required.

Conventional needle and syringe devices have been used to implant a drug depot to sites such as, for example, the epidural space. These devices typically utilize a syringe preloaded with the drug depot and an epidural needle. The needle is inserted through the skin, supraspinus ligament, intraspinus ligament, ligamentum flavum and then into the epidural space. The drug depot is delivered through the needle to the epidural space using the syringe plunger. Conventional needle and syringe devices often do not easily allow controlled and precision implant of the drug depot. If multiple drug depot implants are needed, these conventional needle and syringe devices often do not allow accurate placement of the implant in a manner so that one drug depot does not substantially interfere with the dissolution of the other.

New drug depot devices are needed, which can easily allow accurate and precise implantation of a drug depot with minimal physical and psychological trauma to a patient. When implanting several drug depots, a drug depot device is needed that accurately and precisely allows placement of the drug depot in a manner such that one depot does not substantially interfere with the dissolution of the others.

SUMMARY

New drug depot devices, which can easily allow accurate and precise implantation of a drug depot with minimal physical and psychological trauma to a patient are provided. One advantage of the drug depot device is that it allows the user to dispense multiple doses of the drug in sequence.

The drug depot device, in various embodiments, includes a drug cartridge containing one or more drug pellets that has the advantages of easily being sterilized, the drug cartridge is coupled to a housing, a plunger in order to facilitate the release of the drug depot from the drug cartridge, and a cannula to deliver the drug depot to a site beneath the skin of a patient. In some embodiments, the drug depot device allows the user to "dial-a-dose" to deliver the drug depot. In some embodiments, the device contains a bulking agent and/or covers to hold the drug depot in position within the chambers, which makes for easier and more accurate delivery of the drug depot.

In one embodiment, a drug cartridge is provided for delivering a drug pellet to a site beneath the skin of a patient, the drug cartridge comprising: two or more chambers, each chamber holding a drug pellet and having a proximal end and a distal end, the proximal end of the chamber having an opening to receive the drug pellet and a plunger, the distal end of the chamber having an opening for receiving the plunger and passage of the drug pellet, a bulking agent disposed within at least a portion of each chamber, wherein movement of the plunger to an extended position moves the drug pellet within the chamber of the cartridge out the distal end of the chamber and out of the drug cartridge to the site beneath the skin.

In another embodiment, a drug cartridge is provided for delivering a drug pellet to a site beneath the skin of a patient, the drug cartridge comprising: two or more chambers, each chamber holding a drug pellet and having a proximal end and a distal end, the proximal end of the chamber having an opening to receive the drug pellet and a plunger, the distal end of the chamber having an opening for receiving the plunger and passage of the drug pellet, a biodegradable superior cover disposed on the proximal end of each chamber and a biodegradable inferior cover disposed on the distal end of each chamber, wherein movement of the plunger to an extended position pierces the superior cover, moves the drug pellet out of the distal end of the chamber and pierces the inferior cover of the drug cartridge to deliver the drug pellet to the site beneath the skin.

In yet another embodiment, a method of delivering a drug pellet to a site beneath the skin is provided, the method comprising: inserting a cannula at the target tissue site, the cannula having a proximal end and a distal end, the proximal end of the cannula having an opening to receive a drug pellet, the distal end of the cannula capable of insertion to the site beneath the skin of the patient and having an opening for passage of the drug pellet; and attaching a drug cartridge to the proximal end of the cannula, the drug cartridge comprising: two or more chambers, each chamber holding a drug pellet and having a proximal end and a distal end, the proximal end of the chamber having an opening to receive the drug pellet and a plunger, the distal end of the chamber having an opening for receiving the plunger and passage of the drug pellet, a biodegradable superior cover disposed on the proximal end of each chamber and a biodegradable inferior cover disposed on the distal end of each chamber, wherein movement of the plunger to an extended position pierces the superior cover, moves the drug pellet out of the distal end of the chamber and pierces the inferior cover of the drug cartridge and moves the pellet into the proximal end and distal end of the cannula to the site beneath the skin.

Additional features and advantages of various embodiments will be set forth in part in the description that follows, and in part will be apparent from the description, or may be learned by practice of various embodiments. The objectives and other advantages of various embodiments will be realized and attained by means of the elements and combinations particularly pointed out in the description and appended claims.

BRIEF DESCRIPTION OF THE DRAWINGS

In part, other aspects, features, benefits and advantages of the embodiments will be apparent with regard to the following description, appended claims and accompanying drawings where:

Figure 1:
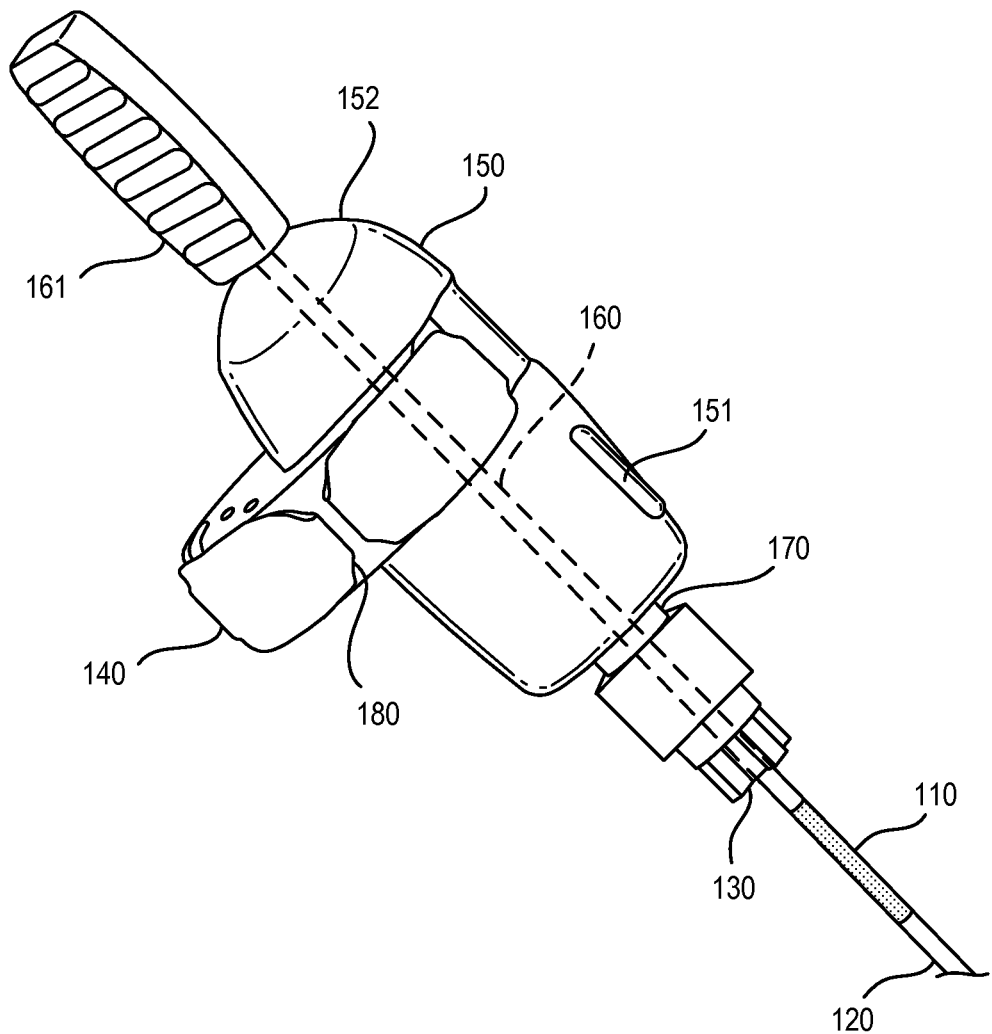
FIG. 1 illustrates the side view of an embodiment of a drug depot delivery device having a cannula and a cartridge for storing a drug depot where the cannula and the cartridge are attached to a housing. In this embodiment, a plunger is inserted through the top of the housing, through the cartridge, and through the cannula for delivering the drug depot to a delivery site.

It is to be understood that the figures are not drawn to scale. Further, the relation between objects in a figure may not be to scale, and may in fact have a reverse relationship as to size. The figures are intended to bring understanding and clarity to the structure of each object shown, and thus, some features may be exaggerated in order to illustrate a specific feature of a structure.

DETAILED DESCRIPTION

For the purposes of this specification and appended claims, unless otherwise indicated, all numbers expressing quantities of ingredients, percentages or proportions of materials, reaction conditions, and other numerical values used in the specification and claims, are to be understood as being modified in all instances by the term "about." Accordingly, unless indicated to the contrary, the numerical parameters set forth in the following specification and attached claims are approximations that may vary depending upon the desired properties sought to be obtained by the present invention. At the very least, and not as an attempt to limit the application of the doctrine of equivalents to the scope of the claims, each numerical parameter should at least be construed in light of the number of reported significant digits and by applying ordinary rounding techniques.

Notwithstanding that the numerical ranges and parameters setting forth, the broad scope of the invention are approximations, the numerical values set forth in the specific examples are reported as precisely as possible. Any numerical value, however, inherently contains certain errors necessarily resulting from the standard deviation found in their respective testing measurements. Moreover, all ranges disclosed herein are to be understood to encompass any and all subranges subsumed therein. For example, a range of "1 to 10" includes any and all subranges between (and including) the minimum value of 1 and the maximum value of 10, that is, any and all subranges having a minimum value of equal to or greater than 1 and a maximum value of equal to or less than 10, e.g., 5.5 to 10.

It is noted that, as used in this specification and the appended claims, the singular forms "a," "an," and "the," include plural referents unless expressly and unequivocally limited to one referent. Thus, for example, reference to "a drug depot" includes one, two, three or more drug depots.

Reference will now be made in detail to certain embodiments of the invention, examples of which are illustrated in the accompanying drawings. While the invention will be described in conjunction with the illustrated embodiments, it will be understood that they are not intended to limit the invention to those embodiments. On the contrary, the invention is intended to cover all alternatives, modifications, and equivalents, which may be included within the invention as defined by the appended claims.

The headings below are not meant to limit the disclosure in any way; embodiments under any one heading may be used in conjunction with embodiments under any other heading.

New drug depot devices, which can easily allow the accurate and precise implantation of multiple drug depots with minimal physical and psychological trauma to a patient are provided. In various embodiments the drug depot device allows the user to dispense multiple drug depots, in sequence, to a site beneath the skin of the patient. In various embodiments, when several drug depots are to be implanted, a drug depot device is provided that accurately allows placement of the drug depot in a manner such that one depot does not substantially interfere with the dissolution of the others. In various embodiments, the drug depot device includes a drug cartridge containing one or more chambers for storing drug pellets, wherein the drug pellets can easily be sterilized and loaded into the drug depot device. In various embodiments, by using the drug cartridge having discrete regions to store delivery pellets, clustering of pellets and mis-delivery of drug pellets is reduced or avoided. In some embodiments, the drug depot device allows the user to "dial-a-dose" to deliver the drug dept. In some embodiments, the device contains a bulking agent and/or covers to hold the drug depot in position within the chambers, which makes for easier delivery of the drug depot.

In one embodiment, a device for delivering a drug depot to a site beneath the skin of patient is provided, the device comprising: a cannula having a proximal end and a distal end, the proximal end of the cannula having an opening to receive the drug depot, the distal end of the cannula capable of insertion to the site beneath the skin of the patient and having an opening for passage of the drug depot; a drug cartridge comprising at least two chambers, wherein each chamber is configured to store and release a drug depot into the cannula when the cannula is aligned with a first chamber; a housing having a top end, a bottom end, and a open portion, wherein the bottom end of the housing has a coupling means for coupling to the proximal end of the cannula and wherein the open portion is configured to receive the cartridge; and a plunger having a handle and a tip adapted for expelling a first drug depot stored in the first chamber, wherein the tip of the plunger is slidably receivable within each of the housing, the first chamber of the cartridge, and the cannula to deliver the first drug depot to the site beneath the skin of the patient when at least the first chamber is aligned with the cannula and the plunger.

FIG. 1 illustrates various embodiments of an assembled drug delivery device comprising a cannula 110 a drug cartridge 140 and a plunger 161 all attached via housing 150. In various embodiments, the cannula 110 has a proximal end 130 and a distal end 120. The distal end of the cannula 120 is capable of insertion to a site beneath the skin and the proximal end of the cannula 130 is capable of engaging a housing 150. In various embodiments, the proximal end of the cannula 130 is engaged to the housing with a coupling means 170, wherein the coupling means can be a luer lock, threading, friction fit fitting, etc. In various embodiments, the cannula is hollow having a sufficient diameter to allow passage of a drug depot and the plunger 160 that facilitates delivery of the drug to the designate site beneath the skin. The plunger 160 has knob 161 with grips for the user to move the plunger. The housing may also have grips 151 for the user to hold the housing and connect the cannula to it. The size of the cannula is dictated by the procedure.

In various embodiments, a cartridge 140, is secured to the housing 150. In various embodiments the cartridge 140 is circular and is adaptable for attaching to the housing 150 at an opening disposed within the housing at 340. In various embodiments the housing has receiving column, which may be rounded and allows the drug cartridge rotate around the receiving column to maintain the drug cartridge perpendicular to the cannula. In some embodiments the receiving column of the housing is perpendicular to the drug cartridge. Various embodiments provide an indicator means 180 to assist in aligning the drug cartridge 140 within the housing 150 so that the plunger 160, when engaged can dispel the drug pellet from the cartridge 140, through the cannula 110 to the drug delivery site.

In various embodiments, the plunger 160 is slideably engaged within the housing 150, the cartridge 140 and the cannula 110 to deliver a drug pellet at the drug delivery site. In various embodiments, the plunger 160 is slideably inserted through an opening at the top of the housing 152, through the drug cartridge 140, dislodging a drug pellet from the drug cartridge 140, pushing the drug pellet through the cannula 110 and delivering the drug pellet through the distal end of the cannula 120 to the delivery site. The plunger 160 may have a knob 161 on one end to assist the user in manipulating the plunger 160, enabling the user to direct the drug pellet to the delivery site. The knob or handle 161 may be provided in various shapes in relative proportion to the size of the assembled delivery device.

Cannula or Needle

The cannula or needle of the drug depot device is designed to cause minimal physical and psychological trauma to the patient. Cannulas or needles include tubes that may be made from materials, such as for example, polyurethane, polyurea, polyether(amide), PEBA, thermoplastic elastomeric olefin, copolyester, and styrenic thermoplastic elastomer, steel, aluminum, stainless steel, nitinol, titanium, metal alloys with high non-ferrous metal content and a low relative proportion of iron, carbon fiber, glass fiber, plastics, ceramics or combinations thereof. The cannula or needle may optionally include one or more tapered regions. In various embodiments, the cannula or needle may be beveled. The cannula or needle may also have a tip style vital for accurate treatment of the patient depending on the site for implantation. Examples of tip styles include, for example, Trephine, Cournand, Veress, Huber, Seldinger, Chiba, Francine, Bias, Crawford, deflected tips, Hustead, Lancet, or Tuohey. In various embodiments, the cannula or needle may also be non-coring and have a sheath covering it to avoid unwanted needle sticks.

The cannula or needle of the drug depot device has a diameter that is larger than the diameter of at least part of the plunger (e.g., tip, middle, etc.) to allow at least part of the plunger to be slidably received within the cannula or needle. In various embodiments, the diameter of the cannula or needle is substantially the same throughout. In other embodiments, the diameter of the needle or cannula becomes smaller approaching the distal end for drug delivery.

The dimensions of the hollow cannula or needle, among other things, will depend on the site for implantation. For example, the width of the epidural space is only about 3-5 mm for the thoracic region and about 5-7 mm for the lumbar region. Thus, the needle or cannula, in various embodiments, can be designed for these specific areas. Some examples of lengths of the cannula or needle may include, but are not limited to, from about 50 to 150 mm in length, for example, about 65 mm for epidural pediatric use, about 85 mm for a standard adult and about 150 mm for an obese adult patient. The thickness of the cannula or needle will also depend on the site of implantation. In various embodiments, the thickness includes, but is not limited to, from about 0.05 to about 1.655. The gauge of the cannula or needle may be the widest or smallest diameter or a diameter in between for insertion into a human or animal body. The widest diameter is typically about 14 gauge, while the smallest diameter is about 25 gauge. In various embodiments the gauge of the needle or cannula is about 17 to about 25 gauge.

In various embodiments, the plunger, cannula or drug depot include markings that indicate location at or near the site beneath the skin. Radiographic markers can be included on the drug depot to permit the user to accurately position the depot into the site of the patient. These radiographic markers will also permit the user to track movement and degradation of the depot at the site over time. In this embodiment, the user may accurately position the depot in the site using any of the numerous diagnostic-imaging procedures. Such diagnostic imaging procedures include, for example, X-ray imaging or fluoroscopy. Examples of such radiographic markers include, but are not limited to, barium, calcium phosphate, and/or metal beads.

In various embodiments, the needle or cannula may include a transparent or translucent portion that can be visualizable by ultrasound, fluoroscopy, x-ray, or other imaging techniques. In such embodiments, the transparent or translucent portion may include a radiopaque material or ultrasound responsive topography that increases the contrast of the needle or cannula relative to the absence of the material or topography.

In various embodiments, the drug depot comprises a drug cartridge containing drug pellets loaded within the chamber of the drug cartridge, when the plunger is moved to the extended position, the drug cartridge will remain within the housing and the chamber of the drug cartridge will guide the tip of the plunger longitudinally and the drug pellet will be released from it when it is in the extended position. A subsequent or second pellet may be administered by repositioning the needle at a target site, removing the plunger so that it is at a position above the drug cartridge, and rotating the drug cartridge at a position horizontal to the plunger and cannula to align the drug chamber and drug depot with the cannula and plunger. The plunger is then slid in a vertical direction within the housing to release the drug depot from the chamber into the cannula where the drug depot can be delivered to the target site by pushing it out the tip of the needle using the plunger. In this way, sequential delivery of a drug can be accomplished. Thus, the above procedure (e.g., repositioning the needle, removing the plunger, rotating the drug cartridge, inserting the plunger, delivering the drug depot) can be repeated multiple times to deliver multiple drug depots to the target tissue site.

In various embodiments, surrounding the opening of the proximal end of the cannula or needle is a generally cylindrical hub having an engagement means (shown as internal threading) for engaging the housing. Engagement means include, but are not limited to, threading, tracks, clips, ribs, projections, and the like that allow a secure connection between the housing and the proximal end of the cannula. For example, in various embodiments the engagement means may be a luer lock connection, where the cannula has mating threads that mate with the threads disposed on or in the housing.

Housing

The housing may be of various shapes including, but not limited to, cylindrical or round such that the housing allows for the affixation to the cannula as well as the drug cartridge and the plunger.

The housing may comprise a variety of materials, such as, for example, polyurethane, polyurea, polyether(amide), PEBA, thermoplastic elastomeric olefin, copolyester, and styrenic thermoplastic elastomer, steel, nitinol, aluminum, stainless steel, titanium, metal alloys with high non-ferrous metal content and a low relative proportion of iron, carbon fiber, glass fiber, plastics, ceramics or combinations thereof.

Like the cannula or needle, in various embodiments, the housing may have dose indicator markings (e.g., numbers, lines, letters, radiographic markers, etc.) to indicate the number of drug depots delivered. In various embodiments, the plunger includes markings that indicate location at or near the site beneath the skin.

The housing may have contours and allow easy grasping of the device during use for insertion of the drug depot. The housing can be angled for right and left hand users or can be generic for both hands. In various embodiments, the housing can comprise an upper opening, a middle opening, and a lower opening. The upper, middle and lower openings allow a plunger to slide through the openings. The middle opening of the housing, in various embodiments, will receive the drug cartridge and the user can align the chamber of the drug cartridge with the upper middle and lower openings so that the plunger can pass through and deliver the drug depot.

Plunger

Although the first end of the plunger is shown as a knob, it will be understood that the knob can be a top, dial, cap, handle or any member that allows the user to utilize the plunger. The plunger has a second end that includes a tip, which is capable of moving the drug depot within the cannula. In other embodiments, the tip of the plunger is sufficiently pointed so that it is capable of insertion to the site beneath the skin of the patient and the cannula or needle is blunted and used to guide the drug depot to the site.

The plunger has a diameter less than the cannula or needle so that it can be slidably received therein. The plunger may be longer, the same size, or smaller in length than the cannula or needle. In embodiments where the plunger extends from the distal end of the cannula or needle, the plunger is usually longer than the cannula or needle. In some embodiments, the tip of the plunger can be sharp or blunt. The sharper tip of the plunger can be used in embodiments where the drug cartridge has superior and inferior covers that the sharp tip of the plunger can pierce.

The plunger may be made from materials, such as for example, polyurethane, polyurea, polyether(amide), PEBA, thermoplastic elastomeric olefin, copolyester, and styrenic thermoplastic elastomer, steel, aluminum, stainless steel, titanium, nitinol, metal alloys with high non-ferrous metal content and a low relative proportion of iron, carbon fiber, glass fiber, plastics, ceramics or combinations thereof. The plunger may optionally include one or more tapered regions.

Like the cannula or needle, in various embodiments, the plunger may have dose indicator markings (e.g., numbers, lines, letters, radiographic markers, etc.) to indicate the number of drug depots delivered. In various embodiments, the plunger includes markings that indicate location at or near the site beneath the skin.

The plunger tip, which may be a complementary shape to the drug pellet, allows the plunger tip to snuggly fit within the end of the drug pellet for easier drug delivery. The drug pellet may have a rounded end for easier insertion at the desired site.

Drug Depot

In various embodiments, the device comprises a drug depot. A drug depot comprises a physical structure to facilitate implantation and retention in a desired site (e.g., a synovial joint, a disc space, a spinal canal, a tissue of the patient, etc.). The drug depot also comprises the drug. The term "drug" as used herein is generally meant to refer to any substance that alters the physiology of the patient. The term "drug" may be used interchangeably herein with the terms "therapeutic agent", "therapeutically effective amount", and "active pharmaceutical ingredient". It will be understood that a "drug" formulation may include more than one therapeutic agent, wherein exemplary combinations of therapeutic agents include a combination of two or more drugs. The drug provides a concentration gradient of the therapeutic agent for delivery to the site. In various embodiments, the drug depot provides an optimal drug concentration gradient of the therapeutic agent at a distance of up to about 1 mm to about 5 cm from the implant site.

Examples of drugs suitable for use in the drug depot, include, but are not limited to an anti-inflammatory agent, analgesic agent, or osteoinductive growth factor or a combination thereof. Anti-inflammatory agents include, but are not limited to, salicylates, diflunisal, indomethacin, ibuprofen, naproxen, tolmetin, ketorolac, diclofenac, ketoprofen, fenamates (mefenamic acid, meclofenamic acid), enolic acids (piroxicam, meloxicam), nabumetone, celecoxib, etodolac, nimesulide, apazone, gold, sulindac or tepoxalin; antioxidants, such as dithiocarbamate, and other compounds such as sulfasalazine[2-hydroxy-5-[-4-[C2-pyridinylamino)sulfonyl]azo]benzoic acid], steroids, such as fluocinolone, cortisol, cortisone, hydrocortisone, fludrocortisone, prednisone, prednisolone, methylprednisolone, triamcinolone, betamethasone, dexamethasone, beclomethasone, fluticasone, protein inhibitors of TNF, such as etanercept, Remicade, IL-1, such as Kineret®, p38, RANK, RANKL or a combination thereof.

Suitable osteoinductive factors include, but are not limited to, a bone morphogenetic protein, a growth differentiation factor, a LIM mineralization protein or a combination thereof.

Suitable analgesic agents include, but are not limited to, acetaminophen, lidocaine, bupivicaine, opioid analgesics such as buprenorphine, butorphanol, dextromoramide, dezocine, dextropropoxyphene, diamorphine, fentanyl, alfentanil, sufentanil, hydrocodone, hydromorphone, ketobemidone, levomethadyl, mepiridine, methadone, morphine, nalbuphine, opium, oxycodone, papavereturn, pentazocine, pethidine, phenoperidine, piritramide, dextropropoxyphene, remifentanil, tilidine, tramadol, codeine, dihydrocodeine, meptazinol, dezocine, eptazocine, flupirtine or a combination thereof. Analgesics also include agents with analgesic properties, such as for example, amitriptyline, carbamazepine, gabapentin, pregabalin, clonidine, or a combination thereof.

A "depot" includes but is not limited to capsules, microspheres, particles, coating, matrices, wafers, pills, pellets or other pharmaceutical delivery compositions. In various embodiments, the depot may comprise a bioerodible, a bioabsorbable, and/or a biodegradable biopolymer that may provide immediate release, or sustained release of the drug. Examples of suitable sustained release biopolymers include but are not limited to poly (alpha-hydroxy acids), poly (lactide-co-glycolide) (PLGA), polylactide (PLA), polyglycolide (PG), polyethylene glycol (PEG) conjugates of poly (alpha-hydroxy acids), poly(orthoester)s (POE), polyaspirins, polyphosphagenes, collagen, starch, pre-gelatinized starch, hyaluronic acid, chitosans, gelatin, alginates, albumin, fibrin, vitamin E analogs, such as alpha tocopheryl acetate, d-alpha tocopheryl succinate, D,L-lactide, or L-lactide-caprolactone, dextrans, vinylpyrrolidone, polyvinyl alcohol (PVA), PVA-g-PLGA, PEGT-PBT copolymer (polyactive), methacrylates, poly (N-isopropylacrylamide), PEO-PPO-PEO (pluronics), PEO-PPO-PAA copolymers, PLGA-PEO-PLGA, PEG-PLG, PLA-PLGA, poloxamer 407, PEG-PLGA-PEG triblock copolymers, SAIB (sucrose acetate isobutyrate) or combinations thereof. As persons of ordinary skill are aware, mPEG may be used as a plasticizer for PLGA, but other polymers/excipients may be used to achieve the same effect. mPEG imparts malleability to the resulting formulations. In various embodiments, the drug depot comprises poly(lactide-co-glycolide) (PLGA), polylactide (PLA), polyglycolide (PGA), D-lactide, D,L-lactide, L-lactide, D,L-lactide-ε-caprolactone, D,L-lactide-glycolide-ε-caprolactone or a combination thereof.

In various embodiments, the drug depot comprises drug pellets loaded with a therapeutically effective amount of the therapeutic agent, wherein the pellets are injected into a synovial joint, a disc space, a spinal canal, or a soft tissue surrounding the spinal canal. In various embodiments, the drug pellets comprise a gel in viscous form and microspheres loaded with a therapeutic agent, wherein the combination of gel and microspheres are positioned into a synovial joint, disc space, a spinal canal, or a soft tissue surrounding the spinal canal of a subject.

A "therapeutically effective amount" is such that when administered, the drug results in alteration of the biological activity, such as, for example, inhibition of inflammation, reduction or alleviation of pain, improvement in the condition, etc. The dosage administered to a patient can be as single or multiple doses depending upon a variety of factors, including the drug's pharmacokinetic properties, the route of administration, patient conditions and characteristics (sex, age, body weight, health, size, etc.), extent of symptoms, concurrent treatments, frequency of treatment and the effect desired.

In one exemplary embodiment, the drug depot is in the form of a pellet. The pellet can be any shape, such as for example, bullet shaped, spherical, substantially spherical, flaked, rod shaped, square, oval, etc. In various embodiments, an aspect ratio (a ratio of the length of the pellet divided by the width found at an angle of 90° in respect to the length) which is less than about 1.4 to about 1.05. The proximal end of the drug pellet may allow the plunger tip to snuggly fit within the proximal end of the drug pellet for easier drug delivery. The distal end of the drug pellet may be rounded for easier insertion at the site.

In various embodiments, the drug pellet comprises a bullet-shaped body that is made from a biodegradable material. In alternative embodiments, the body of the pellet may be made from a non-biodegradable material. A non-biodegradable body could be a porous hollow chamber filled with the therapeutic agent alone or incorporated into a degradable polymer. It may be desirable to make the body non-degradable to be able to retrieve it after it has released its contents. Non-limiting examples of suitable biodegradable materials for the pellet body include polyorthoesters (POE), polylacticglycolic acid (PLGA) polysaccharides (Saber technology), polycapralactone, polyfumarate, tyrosine polycarbonate, etc. The body may be solid, and the therapeutic agent may be dispersed throughout the material that forms the body. The dispersal of the therapeutic agent may be even throughout the body. Alternatively, the concentration of the therapeutic agent may vary throughout the body. As the biodegradable material of the body degrades at the site, the therapeutic agent is released.

Procedures for making pellets include, but are not limited to, extrusion-spheroidization, for spherical pellets where the active pharmaceutical ingredient (API) and any inactive ingredients (excipients, binders, etc.) are pre-mixed, then wetted with water, in a high shear mixer to form a damp mass. The damp mass is then transferred into an extruder where it is forced through a screen or die plate, where it forms an essentially solid, cylindrical extrudate of uniform shape and size. The size of the opening in the screen or die dictate resultant pellet size. The extrudate is fed onto a rotating disk, which may be smooth or may contain a grid (waffled, grooved, etc.) and the extrudate breaks into small cylinders, which in time are rounded into spherically shaped solids. Subsequently, the pellets are dried to the desired residual moisture content, typically in a fluid bed dryer. Any oversized or undersized product is removed by sieving, and the resulting pellets have a narrow size distribution.

In various embodiments, the API is layered on the solid core of the pellet by solution or suspension layering or powder layering techniques. In solution or suspension layering, an API and any inactive ingredients (excipients, binders, etc.) are suspended or dissolved in water or an organic solvent. The resulting liquid is sprayed onto the outside of a core particle, which may include, for example, non-pareil sugar seed (sugar sphere), microcrystalline cellulose pellets and the like, to make the pellet having the desired potency. Solution or suspension layering may be conducted using a wide variety of process techniques, for example, by fluidized bed, Wurster bottom spray techniques, or the like. When the desired potency has been achieved, pellets are dried to the desired residual moisture content. Any oversized or undersized product may be removed by sieving, and the resulting pellets are narrow in size distribution.

Powder layering may also be used to make the drug pellets. Powdered layering involves the application of a dry powder to the pellet core material. The powder may contain the drug, or may include excipients such as a binder, flow aid, inert filler, and the like. In the powder layering technique a pharmaceutically acceptable liquid, which may be water, organic solvent, with or without a binder and/or excipients, is applied to the core material while applying the dry powder until the desired potency is achieved. When the desired potency has been achieved, the pellets may be seal coated to improve their strength, and are then dried to the desired moisture content. Any oversized or undersized product is removed by sieving, and the resulting pellets are narrow in size distribution.

In one embodiment, the pellet is made using a core of biodegradable material, such as, for example, polyglactin, polylactone, polylactide, etc. The core is then coated with a thin layer of the API, such as an anti-inflammatory agent, analgesic agent, etc. by solution, suspension, or powdered layering until the desired potency is achieved.

In various embodiments, the drug pellets can be different sizes, for example, from about 1 mm to 5 mm and have a diameter of from about 0.01 to about 2 mm. The layer or layers will each have a layer thickness of from about 0.005 to 1.0 mm, such as, for example, from 0.05 to 0.75 mm. The drug depot chambers are often larger than the drug depot dimensions to keep the drug depot within the drug chamber.

Like the cannula, needle, or plunger, in various embodiments, the drug depot (e.g., pellet, cartridge, etc.) may have dose indicator markings (e.g., numbers, lines, letters, radiographic markers, etc.) to indicate the number of drug depots delivered. In various embodiments, radiopaque marks are positioned on the depot at opposite ends of the depot to assist in determining the position of the depot relative to the treatment site. For example, the radiopaque marker could be a spherical shape or a ring around the depot.

Drug Cartridge

In various embodiments, the drug depot is stored in a drug cartridge. The drug cartridge comprises one or more chambers, each chamber capable of storing a drug pellet. Each chamber isolates the drug pellet from contact with other drug pellets contained within the cartridge. In this way, overcrowding or multiple pellets in one chamber of the drug cartridge is avoided. Further, drug pellets falling out of the drug cartridge due to limited space in the cartridge is also avoided.

In various embodiments, the drug cartridge is circular having an opening for attaching to the housing structure of the drug depot delivery device. For example, the drug cartridge can be affixed to a column of the housing and the user rotates the cartridge around the housing to align the pellet with the plunger and cannula for delivery. In various embodiments, the drug cartridge is linear and is slidably receivable through the opening of the housing such that the cartridge is perpendicular to the housing. For example, the drug cartridge may be a rectangular shape and slide within the opening of the housing at a position perpendicular to the plunger. To deliver the drug depot, the cartridge slides with the housing to align with cannula and plunger. The plunger then slides through the cannula to deliver the drug depot through the cannula and out to the target site. In various embodiments, the cartridge comprises superior and inferior covers to contain the drug pellet in the chambers to avoid slippage of the pellets from the cartridge.

In various embodiments, the drug cartridge may be made from materials, such as for example, polyurethane, polyurea, polyether(amide), PEBA, thermoplastic elastomeric olefin, copolyester, and styrenic thermoplastic elastomer, steel, aluminum, stainless steel, titanium, metal alloys with high non-ferrous metal content and a low relative proportion of iron, carbon fiber, glass fiber, plastics, ceramics or a combination thereof. In various embodiments, the drug cartridge is not biodegradable.

In some embodiments, the drug cartridge comprises 1, 2, 3, 4, 5, 6, 7, 8, 9, 10, 11, 12, 13, 14, 15, 16, 17, 18, 19, and 20 drug chambers, where each chamber comprises one drug depot. The chambers can be spaced an equal distance from each other. For example, the drug chamber can be spaced 0.5 mm, or 1 mm or 5 mm, or 1 cm to about 2 cm from each other.

In various embodiments, the drug depot is secured within a chamber by a superior surface to cover the top of the drug cartridge and an inferior surface to cover the bottom of the drug cartridge. The superior and inferior covers keep the drug depot in place preventing the drug depot from slipping from the cartridge. In various embodiments, the superior and inferior covers are made from the same material used to make the drug cartridge, or any other exemplary material that could be used to make the drug cartridge.

Figure 4:
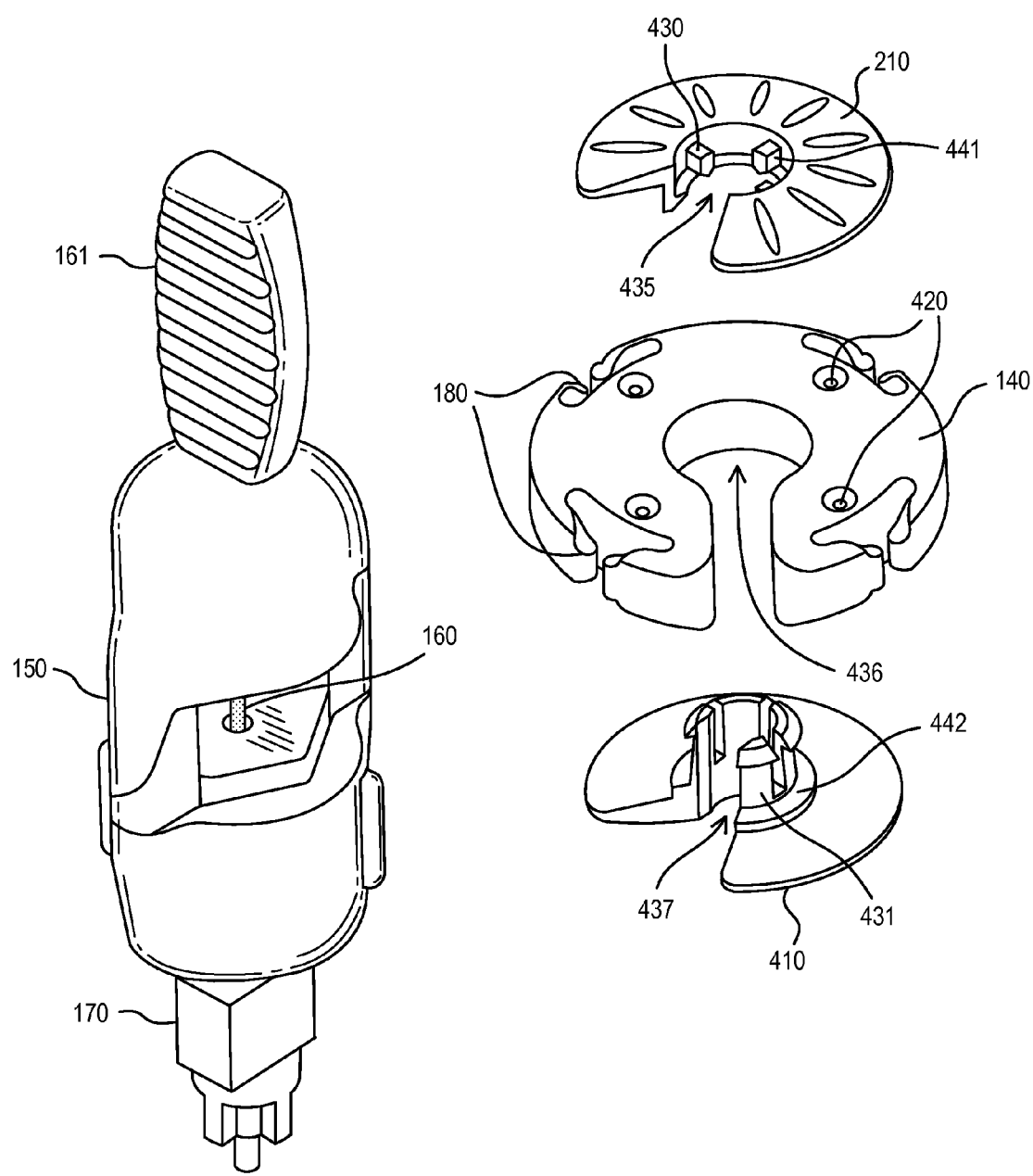
FIG. 4 illustrates an embodiment of a drug delivery device and exploded view of a cartridge for attaching to the drug delivery device. In the illustrated embodiment, the cartridge has a plurality of chambers for storing the drug depot and an indicator along the circumference of the chambers for indicating when the chamber is aligned within the device for delivery of the drug depot. In this embodiment, the cartridge has a superior and an inferior plate for securing the drug depot within the chamber of the cartridge.

In the embodiments of the cartridge where the covers are not penetrable, when the cartridge is affixed to the body of the housing, only the chambers not aligned for delivery of the drug depot are covered by the superior and inferior covers. For example, when the superior and inferior covers are not penetrable by the plunger, they are substantially contiguous with the drug cartridge such that the surface of the superior and inferior cover contacts the drug cartridge, except for the region of the drug cartridge that contacts the housing as this region will be aligned with the plunger and cannula for delivery of the drug depot. In FIG. 4, regions 431 and 435 illustrate regions of the superior and inferior covers that are not contiguous with the drug cartridge.

In various embodiments, the superior cover and the inferior cover securing the drug depot in the chamber in the drug cartridge are made of a thin layer of material that can be penetrated and can be cored by the plunger and/or depot in order to release the drug depot. In various embodiments the penetrable material may comprise, for example, a bioerodible, a bioabsorbable, and/or a biodegradable biopolymer. Examples of suitable materials include but are not limited to poly (alpha-hydroxy acids), poly (lactide-co-glycolide) (PLGA), polylactide (PLA), polyglycolide (PG), polyethylene glycol (PEG) conjugates of poly (alpha-hydroxy acids), mPEG, poly(orthoester)s (POE), polyaspirins, polyphosphagenes, collagen, starch, pre-gelatinized starch, hyaluronic acid, chitosans, gelatin, alginates, albumin, fibrin, vitamin E analogs, such as alpha tocopheryl acetate, d-alpha tocopheryl succinate, D,L-lactide, or L-lactide, ε-caprolactone, dextrans, vinylpyrrolidone, polyvinyl alcohol (PVA), PVA-g-PLGA, PEGT-PBT copolymer (polyactive), methacrylates, poly (N-isopropylacrylamide), PEO-PPO-PEO (pluronics), PEO-PPO-PAA copolymers, PLGA-PEO-PLGA, PEG-PLG, PLA-PLGA, poloxamer 407, PEG-PLGA-PEG triblock copolymers, SAIB (sucrose acetate isobutyrate), wax, agar, agarose, gel-vitamin or combinations thereof. In various embodiments, the superior and/or inferior covers comprise poly(lactide-co-glycolide) (PLGA), polylactide (PLA), polyglycolide (PGA), D-lactide, D,L-lactide, L-lactide, D,L-lactide-ε-caprolactone, D,L-lactide-glycolide-ε-caprolactone or a combination thereof.

In some embodiments, the superior and inferior covers comprise a thin film having a thickness of from about 0.05 mm to about 2 mm, or from about 0.1 to 2 mm in thickness, such that on delivery, the plunger can easily pierce the superior cover and the drug pellet can easily pierce the inferior cover to deliver the drug pellet.

Bulking Agent

In various embodiments, the drug depots are secured in the drug cartridge by use of a bulking agent. The bulking agent may be added to the drug depot to ensure the drug depot is secure within the chamber, such that the drug depot is released when the plunger is engaged to dislodge the drug depot from the cartridge. In some embodiments, the bulking agent is added to the drug chamber before the drug depot is added to the chamber. In some embodiments, the drug depot is added to the drug chamber first and then the bulking agent is added to the chamber. In other embodiments, the bulking agent and the drug depot are added to the drug chamber together.

In some embodiments, the bulking agent can be penetrated and can be cored by the plunger and/or depot in order to release the drug depot. A bulking agent includes an excipient, which provides bulk and structure to the drug depot and holds the drug depot in position within the chamber. In some embodiments, the bulking agent prevents unwanted movement, contaminants (e.g., moisture), and breakage of the drug depot. In some embodiments, the bulking agent fills the space within the chamber so that there is little or no repositioning of the drug depot during delivery. Examples of suitable bulking agents include hydrophilic excipients, such as, water soluble polymers; sugars, such as mannitol, sorbitol, xylitol, glucitol, ducitol, inositiol, arabinitol, arabitol, galactitol, iditol, allitol, maltitol, fructose, sorbose, glucose, xylose, trehalose, allose, dextrose, altrose, lactose, talc, zinc oxide, starch, hydroxyethylstarch (hetastarch), cellulose, cyclodextrins, glycine, fructose, gulose, idose, galactose, talose, ribose, arabinose, raffinose, xylose, lyxose, sucrose, maltose, lactose, lactulose, fucose, rhamnose, melezitose, maltotriose, raffinose, altritol, their optically active forms (D- or L-forms) as well as the corresponding racemates; inorganic salts, both mineral and/or mineral organic, such as, calcium salts, such as the lactate, gluconate, glycerylphosphate, citrate, phosphate monobasic and dibasic, succinate, sulfate and tartrate, as well as the same salts of aluminum and magnesium; carbohydrates, such as, the conventional mono- and di-saccharides as well as the corresponding polyhydric alcohols; proteins, such as, albumin; amino acids, such as glycine; emulsifiable fats or polyvinylpyrrolidone or a combination thereof. Exemplary bulking agents include glycine, mannitol, dextran, dextrose, lactose, sucrose, polyvinylpyrrolidone, trehalose, glucose, wax, agar, agarose, gel-vitamin or combinations thereof. The bulking agent may be in solid, semisolid, or liquid form. In various embodiments, the bulking agent is in a powdered form.

In some embodiments, the particle size of the solid or semi-solid bulking agents range is greater than 10 microns as particles of this size are easily removed by macrophages and other cells of the immune system. In some embodiments, the bulking agent has a particle size from about 10 microns to about 1500 microns in diameter, or from about 150 microns to about 1100 microns in diameter, or from about 500 microns to about 900 microns in diameter. The size of the particles chosen for a particular application will be determined by a number of factors. Smaller particles are easier to inject with a smaller gauge size needle. The size of the particles used in a particular procedure will include consideration of the procedure employed, disease progression, the degree of degradation of the affected region, patient size, the disposition of the patient, and the preferences and techniques of the doctor performing the procedure.

In some embodiments, the bulking agent does not contain a therapeutic agent. In other embodiments, a therapeutic agent may be dispersed throughout the bulking agent and provide immediate release of the therapeutic agent.

In some embodiments, the bulking agent includes a bioerodible, a bioabsorbable, and/or a biodegradable biopolymer like the depot and/or superior and/or inferior covers. Examples of suitable materials include but are not limited to poly (alpha-hydroxy acids), poly (lactide-co-glycolide) (PLGA), polylactide (PLA), polyglycolide (PG), polyethylene glycol (PEG) conjugates of poly (alpha-hydroxy acids), mPEG, poly(orthoester)s (POE), polyaspirins, polyphosphagenes, collagen, starch, pre-gelatinized starch, hyaluronic acid, chitosans, gelatin, alginates, albumin, fibrin, vitamin E analogs, such as alpha tocopheryl acetate, d-alpha tocopheryl succinate, D,L-lactide, or L-lactide, ε-caprolactone, dextrans, vinylpyrrolidone, polyvinyl alcohol (PVA), PVA-g-PLGA, PEGT-PBT copolymer (polyactive), methacrylates, poly (N-isopropylacrylamide), PEO-PPO-PEO (pluronics), PEO-PPO-PAA copolymers, PLGA-PEO-PLGA, PEG-PLG, PLA-PLGA, poloxamer 407, PEG-PLGA-PEG triblock copolymers, SAIB (sucrose acetate isobutyrate) or combinations thereof. In various embodiments, the bulking agent comprises poly(lactide-co-glycolide) (PLGA), polylactide (PLA), polyglycolide (PGA), D-lactide, D,L-lactide, L-lactide, D,L-lactide-ε-caprolactone, D,L-lactide-glycolide-ε-caprolactone or a combination thereof.

The bulking agent can be disposed anywhere around the drug depot. For example, the bulking agent can be disposed in at least a portion of each chamber (e.g., distal end opening, proximal end opening, middle or throughout the drug chamber) so as to hold the drug pellet within the chamber. In some embodiments, the bulking agent holds the drug pellet in position and prevents unwanted movement, contaminants (e.g., moisture), and breakage of the drug pellet. The bulking agent fills the space within the chamber so that there is little or no repositioning of the pellet during drug delivery.

The drug device components (e.g., cannula or needle, plunger, housing, engagement means, etc.) may be lightweight, disposable and sterilizable such that when the device is assembled (e.g., the drug cartridge is attached to the housing), the weight of the device does not substantially increase. In various embodiments, one or more components of the device are sterilized by radiation in a terminal sterilization step in the final packaging. Terminal sterilization of a product provides greater assurance of sterility than from processes such as an aseptic process, which require individual product components to be sterilized separately and the final package assembled in a sterile environment.

Typically, in various embodiments, gamma radiation is used in the terminal sterilization step, which involves utilizing ionizing energy from gamma rays that penetrates deeply in the device. Gamma rays are highly effective in killing microorganisms, they leave no residues nor have sufficient energy to impart radioactivity to the device. Gamma rays can be employed when the device is in the package and gamma sterilization does not require high pressures or vacuum conditions, thus, package seals and other components are not stressed. In addition, gamma radiation eliminates the need for permeable packaging materials.

In various embodiments, the drug cartridge provides the advantages of ease of manufacturing in the terminal sterilization process. If the drug pellets are preloaded in the manufacturing process, gamma radiation may be required at higher doses to sterilize the drug depot loaded in the cannula or needle. This is particularly so when the cannula or needle is made from steel or metal. Thus, to sterilize the loaded depot, the dose of gamma rays must be high enough to penetrate the metal, which may destroy the API in the drug depot. By providing a drug cartridge, for example, made of plastic, the drug cartridge and drug pellets in the cartridge can be sterilized, without destroying the API and then subsequently loaded by the manufacturer or the user (e.g., surgeon, physician, nurse, etc.). Further, loading the drug depot into the drug chamber or cannula is easier. This is particularly so when dealing with multi-dose drug pellets that are relatively small (e.g., 1 mm to 5 mm), the user typically cannot grasp these small pellets and load them into the device. By providing them in a drug cartridge, the user does not have to substantially manipulate the individual drug pellets and the risk of contaminating the pellets particularly with sterilized pellets is reduced.

In various embodiments, electron beam (e-beam) radiation may be used to sterilize one or more components of the device. E-beam radiation comprises a form of ionizing energy, which is generally characterized by low penetration and high-dose rates. E-beam irradiation is similar to gamma processing in that it alters various chemical and molecular bonds on contact, including the reproductive cells of microorganisms. Beams produced for e-beam sterilization are concentrated, highly-charged streams of electrons generated by the acceleration and conversion of electricity. E-beam sterilization may be used, for example, when the drug depot includes a gelatin capsule.

Other methods may also be used to sterilize one or more components of the device, including, but not limited to, gas sterilization, such as, for example, with ethylene oxide or steam sterilization.

In some embodiments, the housing, drug cartridge, and/or cannula are transparent so the user can see the position of the plunger and/or the drug depot in the chamber of the drug cartridge. Thus, indicator markings, in this embodiment, are not needed.

In various embodiments, a kit is provided for delivering a drug pellet to a site beneath the skin of a patient, the kit comprising: a sterilized drug delivery device, comprising: a cannula having a proximal end and a distal end, the proximal end of the cannula having an opening to receive the drug pellet, the distal end of the cannula capable of insertion to the site beneath the skin of the patient and having an opening for passage of the drug pellet; a drug cartridge comprising at least two chambers, wherein each chamber is configured to store and release the drug pellet into the cannula when the cannula is aligned with a first chamber of the drug cartridge; a housing having a top end, a bottom end, and a open portion, wherein the bottom end of the housing has a coupling means for coupling to the proximal end of the cannula and the open portion is configured to receive the cartridge; and a plunger having a handle and a tip adapted for expelling a first drug pellet stored in the first chamber, wherein the tip of the plunger is slidably receivable within each of the housing, the first chamber of the cartridge, and the cannula to deliver the first drug pellet to the site beneath the skin of the patient when at least the first chamber is aligned with the cannula and the plunger.

In various embodiments, a kit is provided which may include additional parts along with the drug depot device combined together to be used to implant the drug depot. The kit may include the drug depot device in a first compartment. The second compartment may include the drug cartridge, and any other instruments needed for the implant. A third compartment may include gloves, drapes, wound dressings and other procedural supplies for maintaining sterility of the implanting process, as well as an instruction booklet. A fourth compartment may include additional cannulas and/or needles. Each tool may be separately packaged in a plastic pouch that is radiation sterilized. A cover of the kit may include illustrations of the implanting procedure and a clear plastic cover may be placed over the compartments to maintain sterility.

In various embodiments, a method is provided for delivering a drug pellet to a site beneath the skin, the method comprising: inserting a cannula at the target tissue site, the cannula having a proximal end and a distal end, the proximal end of the cannula having an opening to receive a drug pellet, the distal end of the cannula capable of insertion to the site beneath the skin of the patient and having an opening for passage of the drug pellet; attaching a drug cartridge to the proximal end of the cannula, the drug cartridge having a chamber containing the drug pellet; and rotating the cartridge to align the drug pellet with the proximal end of the cannula and a plunger, the plunger having a handle and a tip adapted for expelling the drug pellet from the cannula, wherein the tip of the plunger is slidably receivable within the chamber and the cannula to deliver the drug pellet to the site beneath the skin of the patient.

In various embodiments, a method is provided for delivering a drug depot to a site beneath the skin of a patient, the method comprising: assembling a drug delivery device wherein the drug delivery device comprises a cannula having a proximal end and a distal end, the proximal end of the cannula having an opening to receive the drug depot, the distal end of the cannula capable of insertion to the site beneath the skin of the patient and having an opening for passage of the drug depot; a cartridge comprising at least a first secure chamber and a second secure chamber, wherein each chamber is capable of storing one drug pellet; a housing having a top end, a bottom end, and an open portion, wherein the bottom end of the housing has a coupling means for coupling to the proximal end of the cannula and wherein the open center is adaptable to receive the cartridge; a plunger having a knob end and a tip end adaptable for expelling the drug pellet, from each chamber, wherein the tip end is slidably receivable within each of the housing, the cartridge, and the cannula to deliver the drug pellet to the site beneath the skin of the patient; selecting a drug delivery site beneath the skin of the patient; and dispensing the drug pellet from the drug delivery device to a site beneath the skin of the patient.

In various embodiments, the seal between the plunger tip and the cannula or needle can be air tight so that when the cannula or plunger penetrates the skin, at times, fluid (e.g., blood, spinal fluid, synovial fluid, etc.) may be drawn up into the cannula or needle. This fluid will be expelled when the plunger is re-inserted into the cannula or needle and the drug depot is released.

The device may be used for localized and/or targeted delivery of the drug to a patient to treat a disease or condition such as for example, rheumatoid arthritis, osteoarthritis, sciatica, carpal tunnel syndrome, lower back pain, lower extremity pain, upper extremity pain, cancer, tissue pain and pain associated with injury or repair of cervical, thoracic, and/or lumbar vertebrae or intervertebral discs, rotator cuff, articular joint, TMJ, tendons, ligaments, bone muscles, and the like.

In various embodiments, the drug depot device is used to treat pain, or other diseases or conditions of the patient. Pain includes acute pain and neuropathic pain. Acute pain refers to pain experienced when tissue is being damaged or is damaged (e.g., injury, infection, etc.). As contrasted to acute pain, neuropathic pain serves no beneficial purpose. Neuropathic pain results when pain associated with an injury or infection continues in an area once the injury or infection has resolved. Sciatica provides an example of pain that can transition from acute to neuropathic pain. Sciatica refers to pain associated with the sciatic nerve which runs from the lower part of the spinal cord (the lumbar region), down the back of the leg and to the foot. Sciatica generally begins with a herniated disc. The herniated disc itself leads to local immune system activation. The herniated disc also may damage the nerve root by pinching or compressing it, leading to additional immune system activation in the area.

Patients include a biological system to which a treatment can be administered. A biological system can include, for example, an individual cell, a set of cells (e.g., a cell culture), an organ, or a tissue. Additionally, the term "patient" can refer to animals, including, without limitation, humans.

Treating or treatment of a disease refers to executing a protocol, which may include administering one or more drugs to a patient (human or otherwise), in an effort to alleviate signs or symptoms of the disease. Alleviation can occur prior to signs or symptoms of the disease appearing, as well as after their appearance. Thus, "treating" or "treatment" includes "preventing" or "prevention" of disease. In addition, "treating" or "treatment" does not require complete alleviation of signs or symptoms, does not require a cure, and specifically includes protocols that have only a marginal effect on the patient.

"Localized" delivery includes, delivery where one or more drugs are deposited within a tissue, for example, a nerve root of the nervous system or a region of the brain, or in close proximity (within about 10 cm, or preferably within about 5 cm, for example) thereto. "Targeted delivery system" provides delivery of one or more drugs depots in a quantity of pharmaceutical composition that can be deposited at the target site as needed for treatment of pain, inflammation or other disease or condition.

Figure 2:
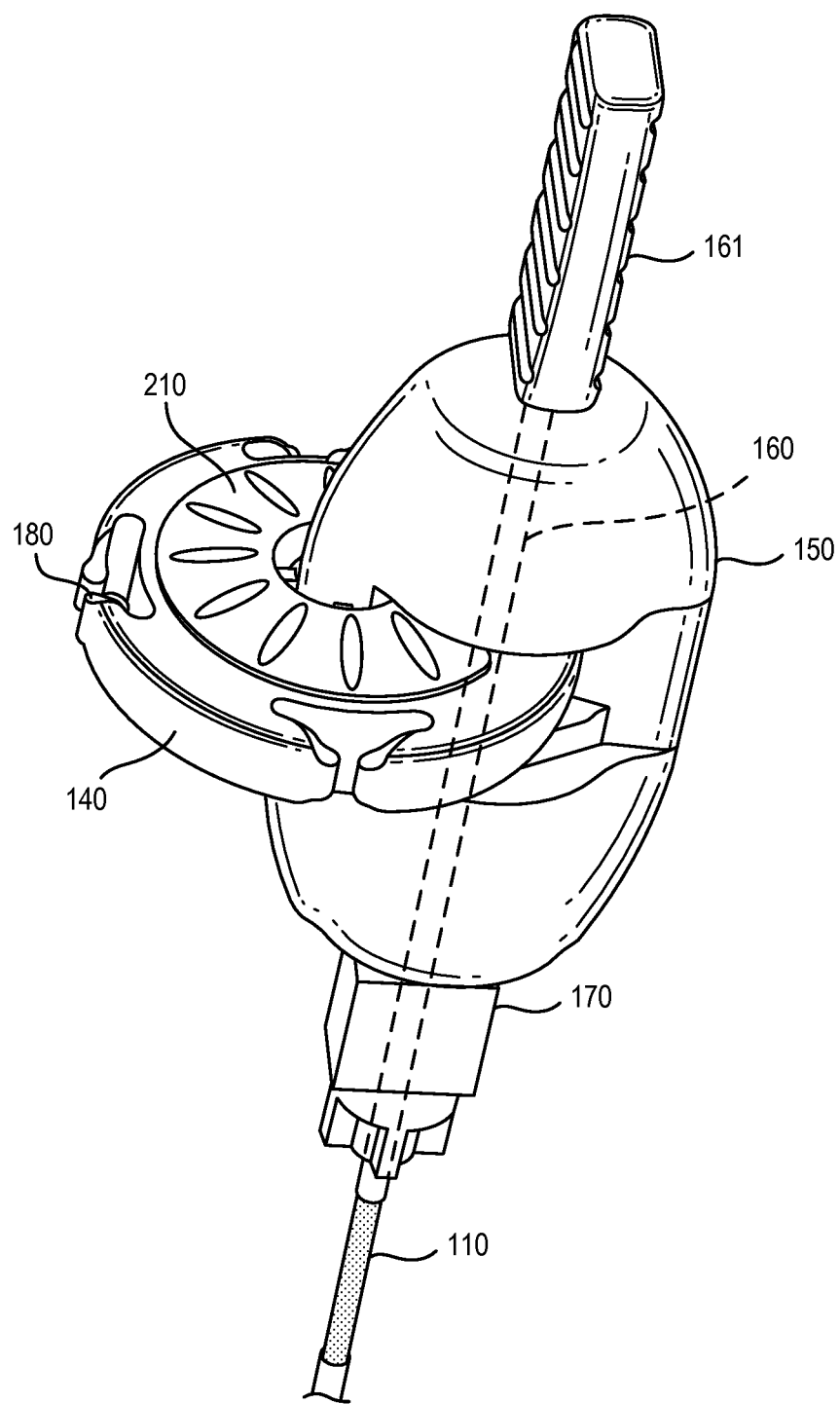
FIG. 2 illustrates top view of an embodiment of the drug depot delivery device having a cannula, a cartridge for storing a drug depot and a plunger for dispensing the drug depot from the cartridge to a drug depot delivery site. This embodiment illustrates the upper containment plate of the cartridge that secures the drug depot inside the cartridge and an indicator means along the outer circumference of the cartridge, which serve to indicate alignment of the drug cartridge for dispensing the drug depot.

FIG. 2 illustrates radial and sectional views of various embodiments of a drug delivery device. In various embodiments the housing 150 is cylindrical and comprises an opening, adaptable for allowing the drug cartridge 140 to attach to the housing 150. In various embodiments, the drug cartridge is circular having an indicator 180 on the outer circumference of the cartridge 140. In various embodiments, the indicator is one or more prongs. In various embodiments, a portion of the drug depot attaches to an opening disposed in the housing to allow rotation of the cartridge about the housing. The prong of the indicator 180 snap fits or locks into place when the drug chamber is aligned with the cannula and plunger 160 so as to allow delivery of the pellet out the cannula 110 by moving the plunger knob 161 in a downward direction. The cannula may be attached to the housing by leur fitting 170.

Various embodiments of the drug cartridge 140 have a superior cover 210 and an inferior cover (not visible) to secure the drug pellets within the cartridge. The superior cover 210 can run continuously on the top of the drug cartridge to cover the drug pellet chambers that are not aligned with the plunger or cannula. In this way, the superior cover holds the drug pellets in position before the drug pellets are delivered.

Figure 3:
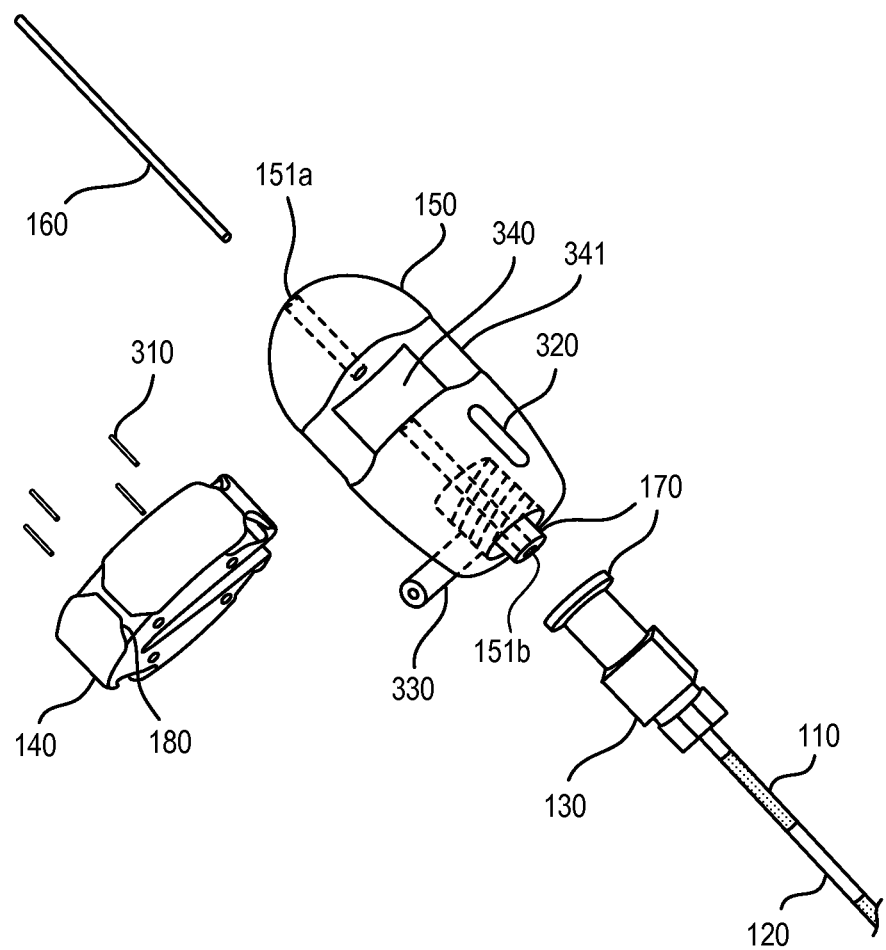
FIG. 3 illustrates an exploded view of an embodiment of a drug depot delivery device having a cannula, a housing, a plunger, and a cartridge for storing a drug depot. In this illustrated embodiment, the housing has a port for injecting or withdrawing liquid.

FIG. 3 illustrates an exploded view of a drug delivery device. In various embodiments, the housing 150 comprises an access port 330 for delivery or removal of liquid material (e.g., NS, LR, D5W, SWFI, blood, etc.). The access port connects to the cannula in as a y connector and allows the user to deliver and withdraw liquid material. Contours 320 are for gripping the device. In FIG. 3, the housing 150 has upper hole 151a, which is a diameter that can receive the plunger. Aligned with hole 151a, is hole 151b, which is a diameter to receive the plunger 160 and one or more drug pellets 310. Cannula 110, proximal end 130, and distal end 120 will also be a diameter to receive the drug pellet and plunger.

In various embodiments, the housing 150 is cylindrically shaped and has an opening in the center 340. Leaving the housing 150 are two columns 341, one on each side of the opening in the center of the housing 340. The opening 340 is adaptable to receiving the cartridge 140 and the columns 341 are adaptable for attaching to the cartridge 140. Both columns 341 may be structurally the same in terms of size and shape, allowing the cartridge 140 to be attached to either column 341 interchangeably.

More particularly, the housing 150 comprises column 341 and opening 340. Column 341 provides a surface for the drug cartridge 140 to rotably attach thereto as the round column 341 provides an axis 140 to fit a portion of the drug cartridge and allow turning and alignment of the cartridge chamber and the drug pellet loaded therein. Projection indicator or index marking 180 allows the drug cartridge to be held in position so that the user knows when the drug pellet 310 is aligned with the holes 151a and 151b of the housing and the cannula for drug delivery.

In various embodiments, the cartridge 140 is circular and is adaptable for attaching to the housing 150. The cartridge 140 is capable of storing drug pellets 310 separately in each chamber.

FIG. 4 illustrates an embodiment of a drug housing 150 and an exploded view of a drug cartridge 140. In various embodiments, the drug cartridge 140 is circular shape having an opening 436 adaptable for attaching to a column of a housing 150. In some embodiments, the opening 436 mates with the column of the housing to provide a friction fit or snap fit so the drug cartridge snaps in position and is rotably disposed around the housing.

Various embodiments of the cartridge 140 comprise multiple chambers 420, each chamber capable of storing a drug pellet for delivery to a site beneath the skin of a patient. The location of the chamber 420 inside the cartridge 140 is indicated by an indicator means 180 along the outer circumference of the cartridge 140.

In various embodiments, the drug pellets are secured in the chamber 420 by use of a superior cover 210 and an inferior cover 410. The superior cover 210 and the inferior cover 410 are affixed about the cartridge 140 such the drug pellets are secured within each chamber 420 and isolated from contact with any other chamber 420 or drug pellet. In various embodiments, the superior cover 210 is directly affixed to the inferior cover 410.

In various embodiments the superior cover 210 and the inferior cover 410 comprise interlocking means, such as prongs, to affix the covers together. The interlocking means 430 are located around the interior opening 441 of the superior cover 210 and around the interior opening of 442 of the inferior cover. The interlocking means 430 of the superior cover 210 and the inferior cover 410 may fit together by any means of securely affixing the superior cover 210 and inferior cover 410. These include mating recesses and/or projections disposed on the inferior and superior covers that secure the cover together in the center, yet allow rotation of the cartridge around the housing column.

For example, in FIG. 4 interlocking means 430 (shown as a projection) is located around the interior opening 441 of the superior cover 210 and around the interior opening of 442 (shown as a recess) of the inferior cover. The projection 430 of the superior cover 210 to the inferior cover 410 may fit together via recess 442 to securely affix the superior cover 210 and inferior cover 410. The projections snap fit or friction fit into the recesses disposed around the inner circumference of the drug cartridge. When affixed together the superior and inferior covers hold the drug pellets in place. The covers interlock with each other via the recesses and/or projections. However, the drug cartridge can still rotate, but the covers do not rotate.

In the embodiments of the cartridge where the covers are not penetrable, shown in FIG. 4, when the cartridge is affixed to the body of the housing, only the chambers not aligned for immediate delivery of the drug depot are covered by the superior 210 and inferior covers 410. For example, when the superior 210 and inferior 410 covers are not penetrable by the plunger, they are substantially contiguous with the drug cartridge 140 such that the surface of the superior and inferior cover contacts the drug cartridge, except for the region of the drug cartridge 436 that contacts the housing as this region will allow the drug cartridge to rotate around the axis of the housing column and be aligned with the plunger 160 and cannula for delivery of the drug depot. Thus regions 435 of the superior cover and 437 of the inferior cover will not cover the drug cartridge 140, when the drug depot is aligned for delivery. The user pushes plunger knob 161 in a downward direction to deliver the drug depot to the target tissue site. It should be noted that the housing can be connected to the cannula by fitting 170.

Figure 5:
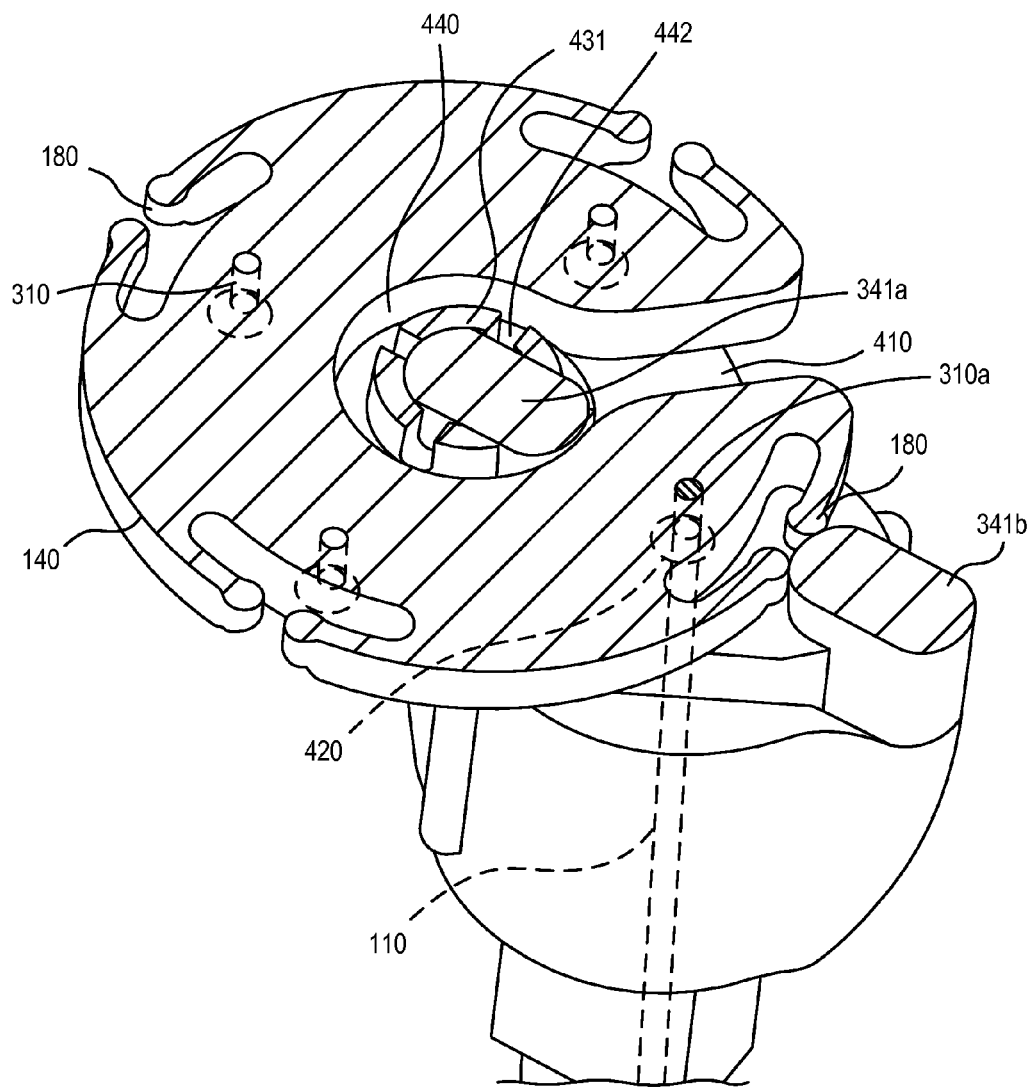
FIG. 5 illustrates a cross-section view of the lower half of an embodiment of a drug delivery device having a cartridge for storing drug depots, the cartridge is attached to the housing of the drug delivery device.

FIG. 5 illustrates a cross section view of an embodiment of a drug delivery device. Various embodiments of the drug delivery device comprise, a drug cartridge 140, having an opening 440 for attaching to a column 341a of the housing of the drug delivery device. The opening 440 mates with column 341a of the housing via a friction fit or snap fit that allows the drug cartridge to rotate around the axis of column 341a. In this way, the user can turn the drug cartridge clockwise or counterclockwise to align drug pellet 310a in chamber 420 so that pellet 310a can now be pushed longitudinally through cannula 110 by a plunger and out to the target tissue site. Indicator means 180 are prongs that maintain alignment of the chamber 420 with the plunger and the cannula to allow delivery of the drug. The indicator means 180 bias and provides friction against opposing column 341b of the housing so that on turning the drug cartridge, the user knows that the drug pellet is ready for delivery as the prongs from indicator means 180 contacts the housing column 341b and stops the chamber when it is aligned with the cannula and plunger. In various embodiments, the indicator means can be identified with dose marking or other markings to give a visual signal to the user that the drug pellet is ready for administering. In various embodiments, the delivery device (e.g., housing, cartridge, covers, etc.) can be transparent for the user to see when the drug pellet is aligned.

In various embodiments, the drug cartridge 140 contains drug pellets 310 stored within a chamber that are secured by superior cover 210 (shown in FIG. 2) and an inferior cover 410. In various embodiments, the superior cover 210 (shown in FIG. 2) and the inferior cover 410 mate with each other using mating projections and/or recesses that interlock with each other so as to provide friction fit to secure the inferior cover 410 and superior cover 210 to allow rotation of the drug cartridge, while the inferior and superior cover remain stationary because they are locked together.

In various embodiments, the housing 150 and the cartridge 140 are attached to the column of the housing 341a by inserting it through the opening of the cartridge 440. In various embodiments, the cartridge 140 is rotatable about the column of the housing 341a to position the chamber 420 of the cartridge 140 containing a drug pellet 310 for dispensing the drug pellet 310 through the cannula 110 to the delivery site. In various embodiments, alignment of the chamber of the cartridge 140 containing the drug pellet 310 with the plunger 160 and the cannula 110 is indicated when the indicator means 180 makes contact with the second column 341b of the housing 150. In various embodiments, the indicator means 180 are prongs that maintain alignment of the chamber 420 with the plunger and the cannula to allow delivery of the drug.

In various embodiments, the drug cartridge 140 rotates about the column 341a, independently of the superior cover plate (not visible) and the inferior cover plate 410, where the cover plates are interlocked with each other and do not rotate with the cartridge 140. In various embodiments, the cover plates remain stationary in order to contain the drug pellets within the drug chamber.

In various embodiments, the interlocking means are located around the opening of the superior cover (not shown) and the interlocking means 431 are located around the opening 442 of the inferior cover 410 and connect securely with each other. The interlocking means 431 create a snug fit about the column of the housing 341 locking the superior and inferior cover plates together to prevent the rotation of the cover plates as the cartridge 140 is rotated to dispense the drug pellet 310 to the delivery site. In various embodiments, the cartridge 140 is rotated about the interlocking means 431, which secure the superior cover and the inferior cover 410 to the column of the housing 341.

Figure 5A:
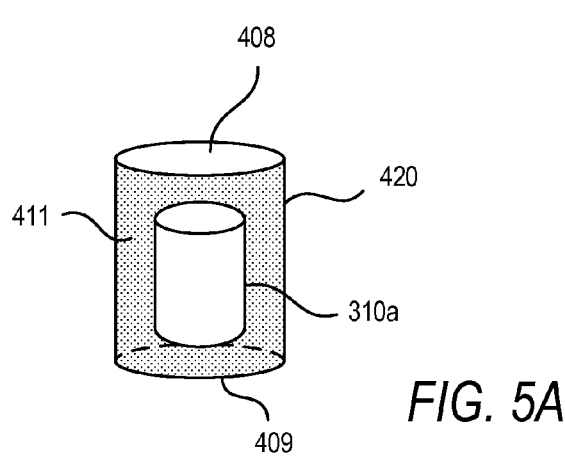
FIG. 5A illustrates a cross-section view of the drug cartridge chamber filled with a bulking agent to fill the voids in the chamber and hold the drug pellet in position.

FIG. 5A illustrates an expanded view of a drug pellet 310a that is loaded in chamber 420 substantially perpendicular to housing of the drug cartridge. In this way the drug pellets are in an upright position within the chamber. Upper opening or proximal opening 408 of the chamber is of a diameter to receive a plunger and drug pellet and lower opening or distal opening 409 is of a diameter to allow exit of the drug pellet and plunger. In some embodiments, the drug pellet is snuggly fit within the chamber so that some force may be required by the plunger to push the drug pellet out of the chamber. In some embodiments, optionally there is a bulking agent shown as 411 that surrounds at least a portion or all of the drug pellet. For example, the bulking agent can be disposed in at least a portion of each chamber (e.g., distal end opening 408, proximal end opening 409, middle portion or throughout the drug chamber as shown in FIG. 5A) so as to hold the drug pellet within the chamber. In some embodiments, the bulking agent holds the drug pellet in position and prevents unwanted movement, contaminants (e.g., moisture), and breakage of the drug pellet. The bulking agent fills the space within the chamber so that there is little or no repositioning of the pellet during drug delivery. It will be understood by those of ordinary skill in the art that the bulking agent can be disposed in discrete regions of the drug chamber and not in others. For example, the bulking agent can be disposed only around the drug depot in the upper part of the chamber or distal end opening 408 or lower part of the chamber or proximal end opening 409 to prevent unwanted movement of the drug pellet before or during drug delivery.

Figure 6:
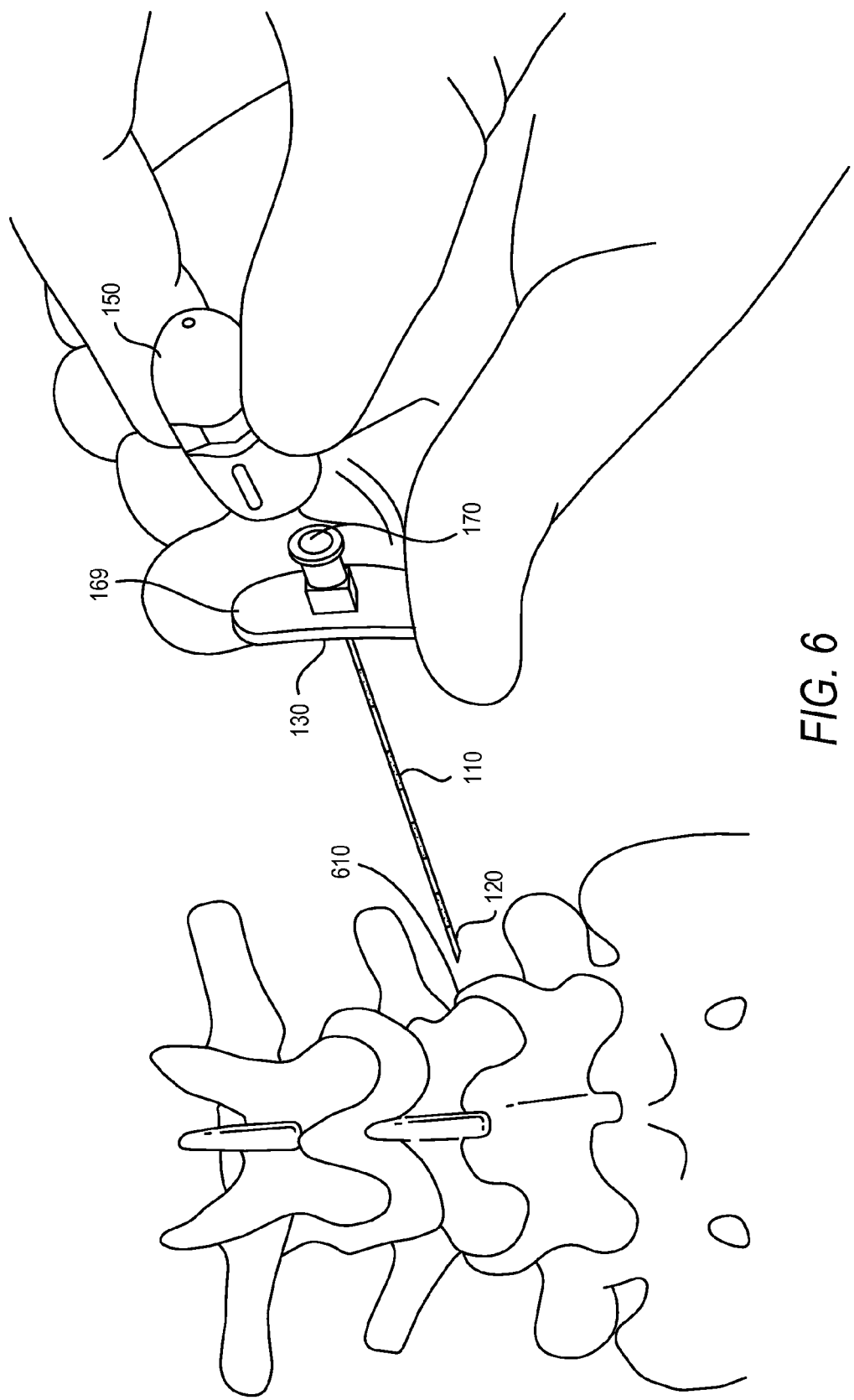
FIG. 6 illustrates an embodiment of the assembly of a drug delivery device where the housing is being coupled to the proximal end of the cannula.
Figure 7:
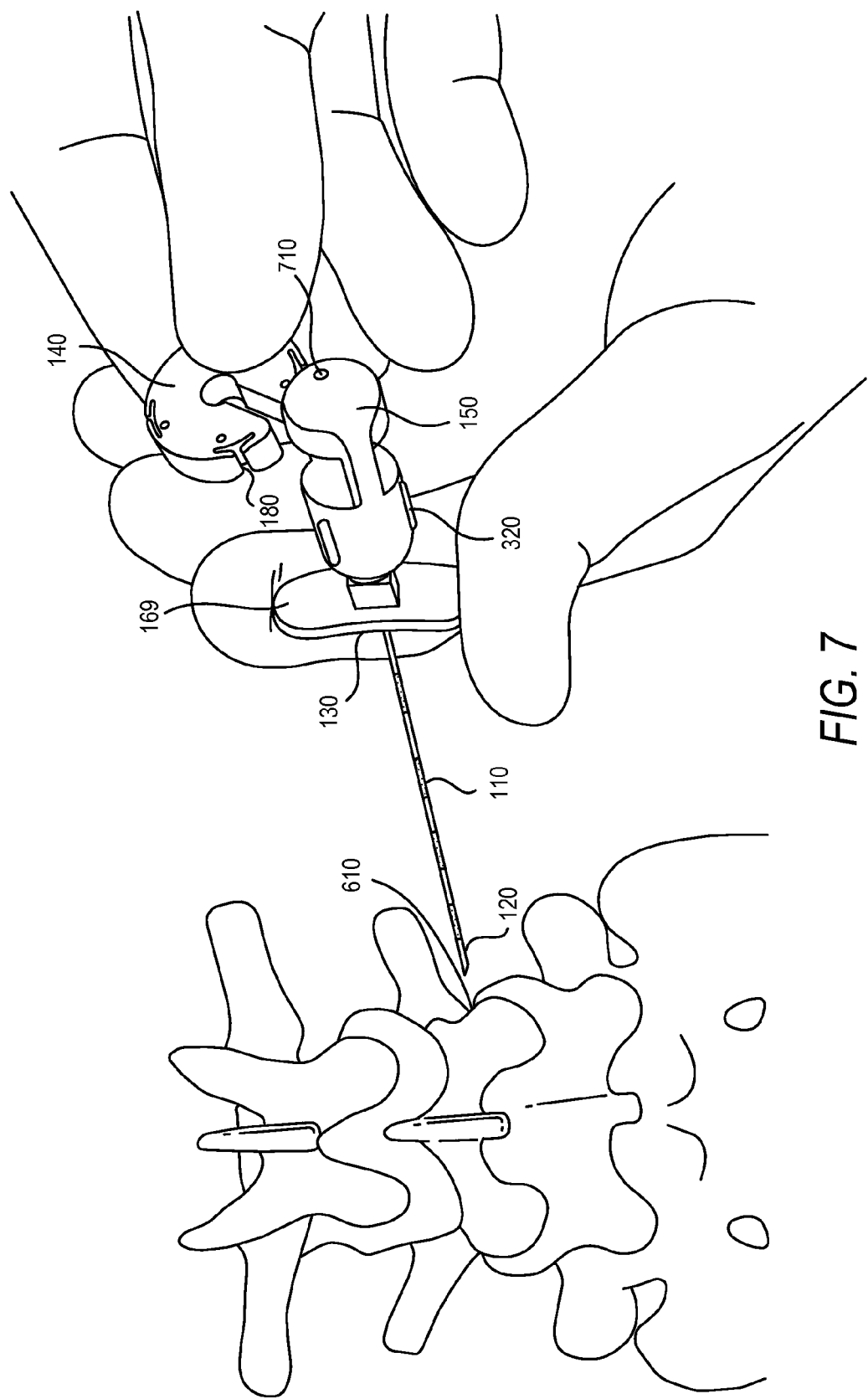
FIG. 7 illustrates an embodiment of the assembly of a drug delivery device where the cartridge is attached to the housing of the drug delivery device.
Figure 8:
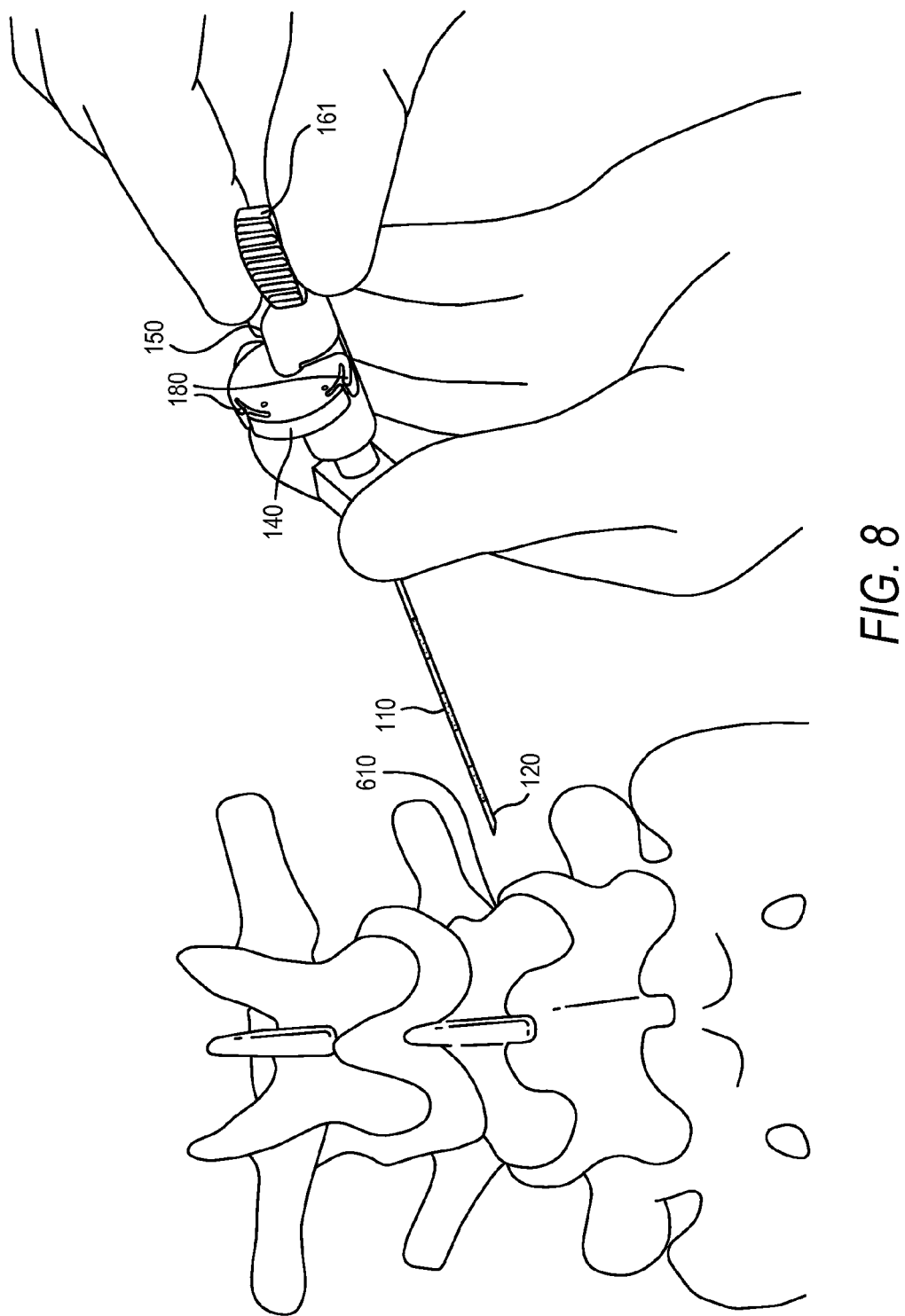
FIG. 8 illustrates an embodiment of the assembly of a drug delivery device where the plunger is inserted into the top of the housing to dispense the drug depot from the cartridge, through the cannula to a drug depot delivery site.

FIGS. 6-8 illustrate exemplary embodiments of application of a drug delivery device being assembled and having a cannula 110 coupled, by a coupling means 170 to a housing 150. In the exemplary embodiments shown, the distal end of the cannula 120 is positioned to deliver the drug depot to a delivery site beneath the skin of a patient 610. The cannula or needle 110 can have wings 169 around it for ease of placement of the needle or cannula and placement of the device at the target tissue site. It will be understood by those of ordinary skill in the art that after delivery of the first drug pellet, the cannula or needle can be re-positioned and another pellet can be delivered to the target area. Thus, the device allows for sequential delivery of multiple pellets and one can triangulate these pellets around a pain generator or other target tissue site. For example, if a target tissue site generates pain, the physician can place multiple drug pellets containing an anti-inflammatory and/or analgesic agent around this pain generator.

In FIG. 7 the cartridge 140 is being affixed to the body of the housing 150. The cartridge can be affixed, for example, to the housing column (not shown). When disposed on the housing column, the drug cartridge will be able to be rotated about the housing column and the user rotates the cartridge clockwise or counterclockwise to align the drug pellet and the chamber so that the housing column will contact the indicator 180, which will let the user know that the pellet is aligned and in position for delivery. Shown in FIG. 7, the housing 150 is attached to the cannula or needle 110 by attachment means, such as for example, a luer-lock connection. The cannula or needle 110 will align with the housing 150 and plunger hole 710 of the housing. To deliver the drug depot, the user slides the plunger through hole 710 to push the drug pellet out the distal end of the cannula or needle 120 to the target tissue site 610 (shown as a portion of the spine). The user can grip the cannula with wings or handles 169 and the housing around grips 320. In FIG. 8 the plunger is fully inserted into the housing (the plunger knob or head 161 is shown) such that the drug depot is released from the cartridge 140 and delivered through the cannula 110 and delivered at a target tissue site 610 in this case, the spine.

Figure 9:
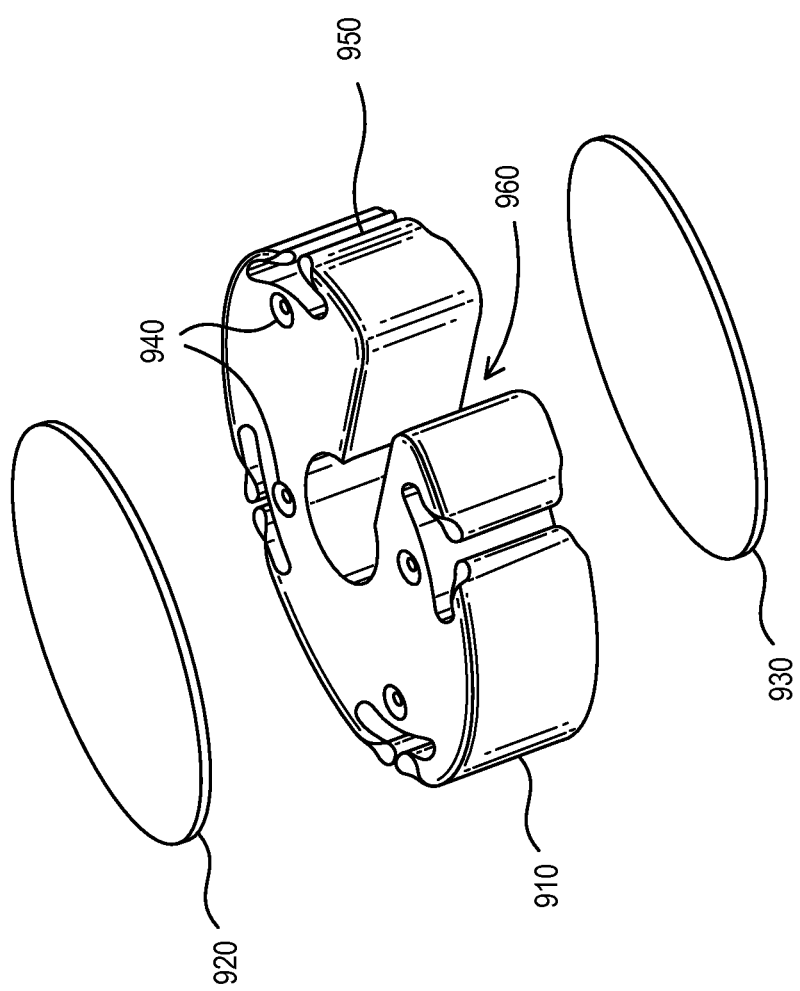
FIG. 9 illustrates an embodiment of a cartridge for storing a drug depot. In this embodiment, the cartridge has internal chambers for storing the drug depot and a superior and inferior plate for securing the drug depot in place. The exterior circumference has indicator means to indicate when the chamber is aligned within the drug delivery device for delivering the drug depot to a delivery site.

FIG. 9 illustrates an embodiment of the drug cartridge 910 having a circular shape and an opening 960 for attaching to a housing. The opening of the drug cartridge 960 is sized to receive a housing column and allows rotation around the housing column to align the holes of the drug depot chamber, with the cannula or needle, and the plunger to allow the plunger to slide throughout the device and deliver the drug pellet. In various embodiments the cartridge 910 contains multiple chambers 940, each chamber capable of storing a drug depot for delivery. In various embodiments, the outer circumference of the chamber comprises indicator means 950 (e.g. prongs and/or recesses) that indicate when the drug chamber is aligned to deliver the drug depot to the delivery site.

In some embodiments the superior cover 920 and the inferior cover 930 secure the drug pellets within the chamber 940 so that the pellets are confined within the chamber. In some embodiments, the superior cover and inferior cover can over lay the top and bottom of the drug cartridge. Thus, there is no need for an opening as with the superior and inferior covers. In some embodiments, the superior cover and inferior cover can be attach to the drug cartridge by any suitable means, such as for example, friction fit, snap-fit, adhesive, clip, hook, weaves, sheet, or wrap on or in the upper and lower surfaces of the drug depot.

In various embodiments the superior cover 930 and the inferior cover 930 comprise a pierceable material so that the device used to expel the drug pellet from the cartridge (e.g. a plunger) is capable of piercing the superior cover 930 and forcing the drug pellet from the chamber 940, piercing also the inferior cover 930 through an attached delivery mechanism (e.g. a cannula or a needle) to a designated delivery site. In some embodiments, on delivery of the drug pellet, a small amount of the superior and inferior cover that was pierced will also be delivered to the target tissue site (e.g., a coring of the covers by the plunger). However, since the covers can be made of biodegradable, non-toxic material, this will not cause harm to the patient.

It will be apparent to those skilled in the art that various modifications and variations can be made to various embodiments described herein without departing from the spirit or scope of the teachings herein. Thus, it is intended that various embodiments cover other modifications and variations of various embodiments within the scope of the present teachings.

What is claimed is:

1. A drug cartridge for delivering at least one drug pellet to a site beneath the skin of a patient, the drug cartridge comprising:

two or more chambers, each chamber holding a drug pellet and having a proximal end and a distal end, the proximal end of the chamber having an opening to receive the drug pellet, and a plunger, the distal end of the chamber having an opening for receiving the plunger and passage of the drug pellet, and a handle disposed above and contacting the plunger and the handle disposed above a housing, a bulking agent contacting an interior portion of each chamber and being external to the drug pellet held in each chamber so as to fill each chamber to prevent each drug pellet from repositioning itself therein during delivery of the drug pellet to the site beneath the skin, and at least two indicators, each indicator having two prongs on an outer surface of the drug cartridge, each of the at least two indicators configured for engagement with the housing, wherein movement of the handle in a downward direction moves the plunger to an extended position, which moves the drug pellet within the chamber of the cartridge out the distal end of the chamber and out of the drug cartridge to the site beneath the skin.

2. A drug cartridge for delivering a drug pellet according to claim 1, wherein the bulking agent is disposed throughout the drug chamber so as to hold the drug pellet within the chamber.

3. A drug cartridge for delivering a drug pellet according to claim 1, wherein the bulking agent is disposed at the proximal end or the distal end of the chamber so as to hold the drug pellet within the chamber.

4. A drug cartridge for delivering a drug pellet according to claim 1, wherein the bulking agent comprises glycine, mannitol, dextran, dextrose, lactose, sucrose, polyvinylpyrrolidone, trehalose, glucose, wax, agar, or a combination thereof.

5. A drug cartridge for delivering a drug pellet according to claim 1, wherein the bulking agent is a powder.

6. A drug cartridge for delivering a drug pellet according to claim 1, wherein the cartridge comprises an opening configured to rotably attach the cartridge to the housing, the housing configured to receive the drug pellet and align with the chamber, a cannula attached to the housing and a plunger slidably receivable within each of the housing, the chamber, and the cannula to deliver the drug pellet to the site beneath the skin of the patient when at least the handle is moved in a downward direction, and the chamber is aligned with the housing, cannula and the plunger.

7. A drug cartridge for delivering a drug pellet according to claim 1, wherein the cartridge comprises an opening configured to rotably attach to the cannula, and wherein the cartridge allows for alignment of each chamber containing the drug pellet with the plunger to deliver the drug pellet through the cannula to the site beneath the skin of the patient.

8. A drug cartridge for storing drug pellets according to claim 1, wherein the drug pellet is between 0.5 mm and 0.8 mm in diameter.

9. A drug cartridge for storing drug pellets according to claim 1, wherein the drug pellets are between 3 mm and 6 mm in length.

10. A drug cartridge for delivering a drug pellet according to claim 1, wherein the bulking agent has a particle size from about 10 microns to about 1500 microns in diameter.

11. A drug cartridge for delivering a drug pellet according to claim 1, further comprising a pierceable biodegradable cover disposed on the proximal or distal end of each chamber so as to completely cover the opening in the proximal or distal end.

12. A drug cartridge for delivering at least one drug pellet to a site beneath the skin of a patient, the drug cartridge comprising:

two or more chambers, each chamber holding a drug pellet and having a proximal end and a distal end, the proximal end of the chamber having an opening to receive the drug pellet and a plunger, and a handle disposed above the plunger and contacting the plunger, and the handle disposed above the housing, the distal end of the chamber having an opening for receiving the plunger and passage of the drug pellet, each chamber including a bulking agent contacting an interior portion of each chamber and being external to the drug pellet held therein so as to fill each chamber to prevent each drug pellet from repositioning itself therein during delivery of each drug pellet to the site beneath the skin, a pierceable biodegradable superior cover disposed on the proximal end of each chamber so as to completely cover the opening in the proximal end, a pierceable biodegradable inferior cover disposed on the distal end of each chamber so as to completely cover the opening in the distal end, and at least two indicators, each indicator having two prongs on an outer surface of the drug cartridge, each of the at least two indicators configured for engagement with the housing, wherein movement of the handle in a downward direction moves the plunger to an extended position, which pierces the superior cover, and moves the drug pellet out of the distal end of the chamber and pierces the inferior cover of the drug cartridge to deliver the drug pellet to the site beneath the skin.

13. A drug cartridge for delivering a drug pellet according to claim 12, wherein the superior cover and inferior cover comprise a polymer film.

14. A drug cartridge for delivering a drug pellet according to claim 12, wherein a bulking agent is disposed within at least a portion of each chamber.

15. A drug cartridge for delivering a drug pellet according to claim 14, wherein the bulking agent is disposed throughout the drug chamber so as to hold the drug pellet within the chamber.

16. A drug cartridge for delivering a drug pellet according to claim 14, wherein the bulking agent comprises glycine, mannitol, dextran, dextrose, lactose, sucrose, polyvinylpyrrolidone, trehalose, glucose, wax, agar, or a combination thereof.

17. A drug cartridge for delivering a drug pellet according to claim 14, wherein the bulking agent is disposed at the proximal end or distal end of the chamber so as to hold the drug pellet within the chamber.

* * * * *